United States Patent
Jang et al.

(10) Patent No.: US 9,422,274 B2
(45) Date of Patent: Aug. 23, 2016

(54) OXAZOLIDINONE DERIVATIVES AND COMPOSITION FOR PREVENTING OR TREATING HEPATITIS C CONTAINING THE SAME

(71) Applicants: Sung Key Jang, Seoul (KR); Gyo Chang Keum, Seoul (KR); Eunice Eun-Kyeong Kim, Seoul (KR); Soon Bang Kang, Seoul (KR); Suyeon Yeom, Seoul (KR); Juhyeon Lee, Seoul (KR); SeungGi Lee, Changwon-si (KR); Hee Sun Kim, Naju-si (KR)

(72) Inventors: Sung Key Jang, Seoul (KR); Gyo Chang Keum, Seoul (KR); Eunice Eun-Kyeong Kim, Seoul (KR); Soon Bang Kang, Seoul (KR); Suyeon Yeom, Seoul (KR); Juhyeon Lee, Seoul (KR); SeungGi Lee, Changwon-si (KR); Hee Sun Kim, Naju-si (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 14/539,472

(22) Filed: Nov. 12, 2014

(65) Prior Publication Data
US 2015/0148386 A1    May 28, 2015

(30) Foreign Application Priority Data
Nov. 15, 2013    (KR) ........................ 10-2013-0139232

(51) Int. Cl.
*C07D 413/14* (2006.01)
*A61K 31/422* (2006.01)

(52) U.S. Cl.
CPC .................... *C07D 413/14* (2013.01)

(58) Field of Classification Search
CPC .. C07D 263/22; C07D 263/20; C07D 263/24; C07D 413/06; C07D 263/26; C07D 413/14; A61K 31/422
USPC .................... 548/229, 231; 514/376
See application file for complete search history.

(56) References Cited

U.S. PATENT DOCUMENTS

2010/0215696 A1    8/2010    Jang et al.

FOREIGN PATENT DOCUMENTS

| KR | 10-2010-0007937 | | 1/2010 |
|---|---|---|---|
| SG | 0185169 A1 | * | 11/2012 |
| WO | WO0194342 A1 | | 12/2001 |
| WO | WO/03022824 A1 | | 3/2003 |
| WO | WO03/035648 A1 | | 5/2003 |
| WO | WO2004/048350 A2 | | 6/2004 |
| WO | WO2004/056817 A1 | | 7/2004 |
| WO | WO2005/116022 A1 | | 12/2005 |
| WO | WO2008/021927 A3 | | 2/2008 |
| WO | WO2008021927 A2 | | 2/2008 |
| WO | WO2010/099527 A1 | | 2/2010 |
| WO | WO2004/048350 A3 | | 6/2010 |
| WO | WO2010/096462 A1 | | 8/2010 |
| WO | WO2010/966777 A1 | | 8/2010 |
| WO | WO2010/132538 A1 | | 11/2010 |
| WO | WO 2010132601 | | 11/2010 |
| WO | WO 2010132601 A | | 11/2010 |
| WO | WO2010/148006 A1 | | 12/2010 |
| WO | WO2011156578 A1 | | 12/2011 |

OTHER PUBLICATIONS

Folkert Recket al. Novel Substituted (Pyridin-3-yl)phenyloxazolidinones: Antibacterial Agents with Reduced Activity against Monoamine Oxidase A and Increased Solubility, J. Med. Chem, 2007, 50, 4868-4881.
So-Yeop Han et al., Recent development of peptide coupling reagents in organic synthesis, Tetrahedron, 2004, 60, 2447.
Takashi Komine et al, Synthesis and Structure-Activity Relationship Studies of Highly Potent Novel Oxazolidinone Antibacterials, J. Med. Chem., 2008, 51, 6558-6562.
Norio Miyaura et al., Palladium-Catalyzed Cross-Coupling Reactions of Organoboron Compounds, Chemical Reviews, 1995, 95, 7, 2457-2483.
Min Gao et al., Chemical genetics strategy identifies an HCV NS5A inhibitor with a potent clinical effect, Nature, 2010, 96-1102, 465.
Jin Zhong et al., Robust hepatitis C virus infection in vitro, Jun. 28, 2005, 9294-9299, vol. 102, No. 26.

* cited by examiner

*Primary Examiner* — Alicia L Otton
*Assistant Examiner* — Sagar Patel
(74) *Attorney, Agent, or Firm* — Goldilocks Zone IP Law

(57) ABSTRACT

The present invention relates to oxazolidinone compounds represented by Chemical Formula 1, pharmaceutically acceptable salts thereof or hydrates, a method of preparing the same, and a pharmaceutical composition for preventing or treating Hepatitis C infection:

[Chemical Formula 1]

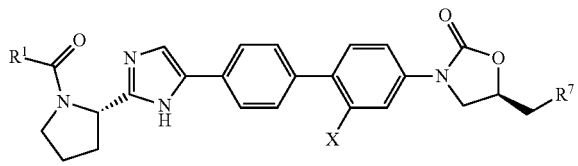

Wherein $R^1$, $R^7$ and X are defined in the detailed description.

20 Claims, No Drawings

OXAZOLIDINONE DERIVATIVES AND COMPOSITION FOR PREVENTING OR TREATING HEPATITIS C CONTAINING THE SAME

CROSS-REFERENCE TO RELATED APPLICATIONS

The present application claims the benefit of Korean Patent Application No. 10-2013-0139232, filed on Nov. 15, 2013, in the Korean Intellectual Property Office, the entire disclosure of which is incorporated herein by reference.

BACKGROUND OF THE INVENTION

1. Field of the Invention

The present invention relates to an Oxazolidinone compound represented by Chemical Formula 1, a pharmaceutically acceptable salt thereof or hydrate, and a method of preparing the compounds, a pharmaceutical composition for preventing or treating Hepatitis C Infection including the compounds, a method of preventing or treating Hepatitis C Infection, and an anti-virus agent for inhibiting a growth or activity of HCV Hepatitis C virus (HCV).

Chemical Formula 1

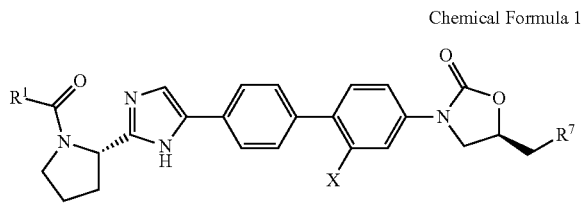

Wherein, $R^1$, $R^7$ and X are defined in the detailed description.

2. Description of the Related Art

Hepatitis C virus (HCV) is very important virus causing Hepatitis C infection, cirrhosis, Hepatocellular carvinoma ((HCC), and a principal cause of chronic Hepatitis C infection in developed countries such as Europe. According to the WHO report, the population infected by HCV is estimated to be about 180,000,000 patients of 3 percent of the world population, and has a yearly increase of 3,000,000 to 4,000,000 patients.

HCV has six genotypes and is widely distributed in the world, but is differently distributed depending on race and region. The patient population infected by infectious HCV increases Genotype 1, 2 and 3 in an orderly matter. HCV Genotype 1 is most difficult to be treated and distributed in Europe and North America. HCV Genotypes 2 and 3 are distributed in the Far East Asia. The patients with HCV Genotype 1 hold a large majority of the patients infected by HCV.

Besides proteins or interferon-based HCV-treating drugs, 10 kinds of small molecular compounds are processed under the clinical trial as a HCV drug, and are inhibiting agents of viral enzyme such as NS3/4A protease and RNA-dependent RNA polymerase (RdRp) and of host enzyme such as NS5B cyclophilin and α-glucosidase. The structures of drug targets such as NS3 protease, NS3 helicase, NS3 protease/helicase complex, NS5B polymerase and the like can provides the structure of enzyme active site, thereby showing the possibility of the structure-based drug development, the structures of various modified enzymes and their structure of the enzyme-drug interaction. The information on an active site of enzyme binding to the drug, allosteric drug, and detection of drug resistance and chemical drug design have accelerated the new drug development.

Any vaccine for preventing or treating HCV infection has not been developed. At present, according to standard HCV treatment method, the injection of PEG-Interferon-alpha injection are provided once in a week, together with oral administration of Ribavirin once in a day, and the treatment is continued for 24 weeks. The combination therapy of PEG-Interferon-alpha and Ribavirin has an efficacy on only 50 percent of patients. In combination with the standard HCV treatment, the combinational administration of Boceprevir (Merck & Co.) approved by FDA on 2011. Which inhibits NS3 NS4A protease of HCV, and Telaprevir (vertex) has increased the therapeutic effect. However, there is no approved drug used for a patient with chronic Hepatitis C infection who have no therapeutic effect to the HCV drug.

In the standard HCV treatment method, no sustained virologic response (SVR) are caused by no drug efficacy, reoccurrence, and drug tolerance. Also, the standard HCV treatment method has various side effects such as influenza-like pain, fever, fatigue, anemia, thrombocytopenia, leukopenia, bald head and depression thereby making continuous treatment in 10 to 15 percent of HCV patients. In particular, the HCV patients who are very difficult to treat have infection of HCV Genotype 1, concurrent infection of HIV and HCV, advanced cirrhosis and live transplant. Therefore, the drug with more efficient treatment effect is still needed.

Accordingly, the present inventors have endeavored to resolve the problems, and thus developed anti-viral compounds having an excellent growth-inhibition activity for HCV infection, specifically oxazolidinone compounds inhibiting the function of HCV NS5A non-structural protein, pharmaceutically acceptable salt thereof, or hydrate, a method of preparing the same, and a pharmaceutical composition for prevention or treatment of HCV infection.

SUMMARY OF THE INVENTION

An object of the present invention is to provide an oxazolidinone compound, pharmaceutically acceptable salt thereof or hydrate.

Another object of the present invention is to provide a method of preparing the oxazolidinone compound, pharmaceutically acceptable salt thereof or hydrate.

Further object of the present invention is to provide a method of preventing or treating a disease related with HCV infection, including administering the oxazolidinone compound, pharmaceutically acceptable salt thereof or hydrate, to a subject in need.

Still further object of the present invention is to provide a method of inhibiting growth or activity of HCV, including treating the oxazolidinone compound, pharmaceutically acceptable salt thereof or hydrate at an amount of anti-virally effective amount.

DETAILED DESCRIPTION OF THE PREFERRED EMBODIMENTS

An embodiment of the present invention is oxazolidinone compound represented by Chemical Formula 1, pharmaceutically acceptable salt thereof, or hydrate:

[Chemical Formula 1]

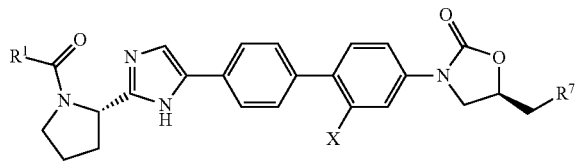

In Chemical Formula 1,
$R^1$ is $C_1$-$C_6$ alkyl, $C_1$-$C_6$ alkoxy or —CH($R^3$)NHCO$_2R^4$,
$R^3$ is $C_1$-$C_6$ alkyl or $C_6$-$C_{10}$ aryl,
$R^4$ is $C_1$-$C_6$ alkyl,
$R^7$ is

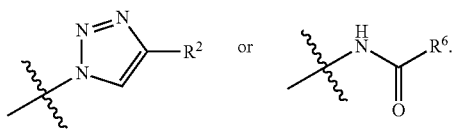

$R^2$ is H, $(CH_2)_n WR^5$ or $C_6$-$C_{10}$ aryl,
n is an integer of 0 or 1 to 4,
$R^5$ is H, $C_1$-$C_6$ alkyl, benzyl, or $C_1$-$C_6$ alkyl carbonyl,
$R^6$ is $C_1$-$C_6$ alkyl,
W is oxygen or nitrogen, and
X is H or F.
For example, the present invention relates to oxazolidinone compound represented by Chemical Formulae 2 or 3, pharmaceutically acceptable salt thereof, or hydrate:

[Chemical formula 3]

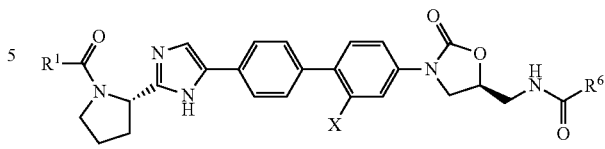

In the Chemical formula 3,
$R^1$ and $R^6$ is independently $C_1$-$C_6$ alkyl, $C_1$-$C_6$ alkoxy or —CH($R^3$)NHCO$_2R^4$,
$R^3$ is $C_1$-$C_6$ alkyl or $C_6$-$C_{10}$ aryl,
$R^4$ is $C_1$-$C_6$ alkyl, and
X is H or F.
Preferably, in the Chemical Formula 3,
$R^1$ and $R^6$ is independently $C_1$-$C_6$ alkyl, $C_1$-$C_6$ alkoxy or —CH($R^3$)NHCO$_2R^4$,
$R^3$ is isopropyl or phenyl, and
$R^4$ is $C_1$-$C_6$ alkyl.
In another embodiment, the examples of compounds represented by Chemical Formula 1 are as follows:
tert-butyl (S)-2-(5-(4'-((R)-5-((1H-1,2,3-triazole-1-yl)methyl)-2-oxoxazolidin-3-yl)-2'-fluoro-[1,1'-biphenyl]-4-yl)-1H-imidazole-2-yl)pyrrolidine-1-carboxylate;
(R)-5-((1H-1,2,3-triazole-1-yl)methyl)-3-(4'-(2-((S)-1-acetylpyrrolidine-2-yl)-1H-imidazole-5-yl)-2-fluoro-[1,1'-biphenyl]-4-yl)oxazolidine-2-on;
methyl ((S)-1-((S)-2-(5-(4'-((R)-5-((1H-1,2,3-triazole-1-yl)methyl)-2-oxoxazolidin-3-yl)-2'-fluoro-[1,1'-biphenyl]-4-yl)-1H-imidazole-2-yl)pyrrolidine-1-yl)-3-methyl-1-oxobutane-2-yl)carbamate;

[Chemical Formula 2]

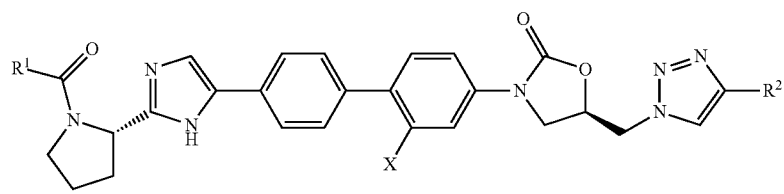

In the Chemical Formula 2,
$R^1$ is $C_1$-$C_6$ alkyl, $C_1$-$C_6$ alkoxy or —CH($R^3$)NHCO$_2R^4$,
$R^2$ is H, $(CH_2)_n WR^5$ or $C_6$-$C_{10}$ aryl,
n is an integer of 0 or 1 to 4,
$R^3$ is $C_1$-$C_6$ alkyl or $C_6$-$C_{10}$ aryl,
$R^4$ is $C_1$-$C_6$ alkyl,
$R^5$ is H, $C_1$-$C_6$ alkyl, benzyl, or $C_1$-$C_6$ alkyl carbonyl,
W is oxygen or nitrogen, and
X is H or F.
Preferably, in the Chemical Formula 2,
$R^1$ is $C_1$-$C_6$ alkyl, $C_1$-$C_6$ alkoxy or —CH($R^3$)NHCO$_2R^4$,
$R^2$ is H, $(CH_2)_n WR^5$ or phenyl,
n is an integer of 1 to 3,
$R^3$ is isopropyl or phenyl,
$R^5$ is H, $C_1$-$C_6$ alkyl, benzyl, or $C_1$-$C_6$ alkyl carbonyl,
W is oxygen or nitrogen, and
X is H or F.

methyl ((S)-2-((S)-2-(5-(4'-((R)-5-((1H-1,2,3-triazole-1-yl)methyl)-2-oxoxazolidin-3-yl)-2'-fluoro-[1,1'-biphenyl]-4-yl)-1H-imidazole-2-yl)pyrrolidine-1-yl)-2-oxo-1-phenylethyl)carbamate;
methyl ((S)-1-((S)-2-(5-(2'-fluoro-4'-((R)-5-((4-(hydroxymethyl)-1H-1,2,3-triazole-1-yl)methyl)-2-oxoxazolidin-3-yl)-[1,1'-biphenyl]-4-yl)-1H-imidazole-2-yl)pyrrolidine-1-yl)-3-methyl-1-oxobutane-2-yl)carbamate;
methyl ((S)-1-((S)-2-(5-(2'-fluoro-4'-((R)-5-((4-(2-hydroxyethyl)-1H-1,2,3-triazole-1-yl)methyl)-2-oxoxazolidin-3-yl)-[1,1'-biphenyl]-4-yl)-1H-imidazole-2-yl)pyrrolidine-1-yl)-3-methyl-1-oxobutane-2-yl)carbamate;
methyl ((S)-1-((S)-2-(5-(2'-fluoro-4'-((R)-5-((4-(methoxymethyl)-1H-1,2,3-triazole-1-yl)methyl)-2-oxoxazolidin-3-yl)-[1,1'-biphenyl]-4-yl)-1H-imidazole-2-yl)pyrrolidine-1-yl)-3-methyl-1-oxobutane-2-yl)carbamate;
(1-(((R)-3-(2-fluoro-4'-(2-((S)-1-((methoxycarbonyl)-L-valyl)pyrrolidine-2-yl)-1H-imidazole-5-yl)-[1,1'-biphenyl]-4-yl)-2-oxooxazolidine-5-yl)methyl)-H-1,2,3-triazole-4-yl)methyl acetate;
methyl((S)-1-((S)-2-(5-(4'-((R)-5-((4-((benzyloxy)methyl)-1H-1,2,3-triazole-1-yl)methyl)-2-oxoxazolidin-3-yl)-2'-fluoro-[1,1'-biphenyl]-4-yl)-1H-imidazole-2-yl)pyrrolidine-1-yl)-3-methyl-1-oxobutane-2-yl)carbamate;

methyl((S)-1-((S)-2-(5-(4'-((R)-5-((4-(acetamidomethyl)-1H-1,2,3-triazole-1-yl)methyl)-2-oxoxazolidin-3-yl)-2'-fluoro-[1,1'-biphenyl]-4-yl)-1H-imidazole-2-yl)pyrrolidine-1-yl)-3-methyl-1-oxobutane-2-yl)carbamate;

methyl((S)-1-((S)-2-(5-(2'-fluoro-4'-((R)-2-oxo-5-((4-phenyl-H-1,2,3-triazole-1-yl)methyl)oxazolidine-3-yl)-[1,1'-biphenyl]-4-yl)-1H-imidazole-2-yl)pyrrolidine-1-yl)-3-methyl-1-oxobutane-2-yl)carbamate;

methyl((S)-1-((S)-2-(5-(4'-((S)-5-(acetamidomethyl)-2-oxazolidine-3-yl)-2'-fluoro-[1,1'-biphenyl]-4-yl)-1H-imidazole-2-yl)pyrrolidine-1-yl)-3-methyl-1-oxobutane-2-yl)carbamate;

tert-butyl(S)-2-(5-(4'-((S)-5-(acetamidomethyl)-2-oxooxazolidin-3-yl)-2'-fluoro-[1,1'-biphenyl]-4-yl)-1H-imidazole-2-yl)pyrrolidine-1-carboxylate;

N—(((S)-3-(4'-(2-((S)-1-acetylpyrrolidine-2-yl)-1H-imidazole-5-yl)-2-fluoro-[1,1'-biphenyl]-4-yl)-2-oxooxazolidine-5-yl)methyl)acetamide;

methyl ((S)-1-((((S)-3-(2-fluoro-4'-(2-((S)-1-((methoxycarbonyl)-L-valyl)pyrrolidine-2-yl)-1H-imidazole-5-yl)-[1,1'-biphenyl]-4-yl)-2-oxooxazolidine-5-yl)methyl)amino)-3-methyl-1-oxobutane-2-yl)carbamate;

tert-butyl (S)-2-(5-(2'-fluoro-4'-((S)-5-(((S)-2-((methoxycarbonyl)amino)-3-methylbutanamido)methyl)-2-oxoxazolidin-3-yl)-[1,1'-biphenyl]-4-yl)-1H-imidazole-2-yl)pyrrolidine-1-carboxylate; and methyl((S)-1-((((S)-3-(4'-(2-((S)-1-acetylpyrrolidine-2-yl)-1H-imidazole-5-yl)-2-fluoro-[1,1'-biphenyl]-4-yl)-2-oxooxazolidine-5-yl)methyl)amino)-3-methyl-1-oxobutane-2-yl)carbamate.

The oxazolidinone compound can be a pharmaceutically-acceptable salt of organic acid or inorganic acid, or hydrate thereof. The preferred salts include at least one selected from the group consisting of hydrochloric acid, hydrobromic acid, sulfuric acid, phosphoric acid, nitric acid, acetic acid, glycolic acid, lactic acid, pyruvic acid, malic acid, succinic acid, glutaric acid, fumaric acid, malonic acid, a mandelic acid, tartaric acid, citric acid, ascorbic acid, palmitic acid, maleic acid, hydroxymaleic acid, benzoic acid, hydroxybenzoic acid, phenylacetic acid, cinnamic acid, salicylic acid, methanesulfonic acid, benzene sulfonic acid and toluene sulfonic acid.

In addition, an embodiment of the present invention relates to a method of preparing the oxazolidinone compounds represented by Chemical Formula 2 or 3, a pharmaceutically acceptable salt thereof or hydrate.

The method of preparing the oxazolidinone compounds represented by Chemical Formula 2 or 3 will be described in detail hereinafter.

Preparation Method 1

Oxazolidinone Compounds of Chemical Formula 2

As illustrated below, the method of preparing an oxazolidinone compound represented by Chemical Formula 2, or a pharmaceutically acceptable salt thereof, comprising a step of reacting the compound of Chemical formula 4 and the compound of Chemical formula 5.

Specifically, the method includes the steps of:

(1) reacting the compound of Chemical formula 4 and the compound of Chemical formula 5 according to the standard Suzuki binding reaction, to produce the compound of Chemical formula 7;

(2) deprotecting Boc protecting group in the compound of Chemical Formula 7 obtained in step (1), to produce the compound of Chemical formula 8; and (3) preparing the compound of Chemical Formula 2 by reacting the compound of Chemical formula 8 with a carboxylic acid derivative according to the standard amide binding:

[Chemical Formula 2]

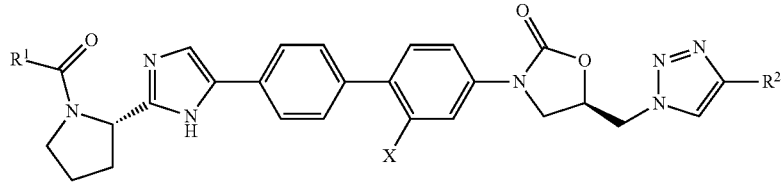

In Chemical Formula 2,
$R^1$ is $C_1$-$C_6$ alkyl, $C_1$-$C_6$ alkoxy or —$CH(R^3)NHCO_2R^4$,
$R^2$ is H, $(CH_2)_n WR^5$ or $C_6$-$C_{10}$ aryl,
n is an integer of 0 or 1 to 4,
$R^3$ is $C_1$-$C_6$ alkyl or $C_6$-$C_{10}$ aryl,
$R^4$ is $C_1$-$C_6$ alkyl,
$R^5$ is H, $C_1$-$C_6$ alkyl, benzyl, or $C_1$-$C_6$ alkyl carbonyl,
W is oxygen or nitrogen, and
X is H or F.

[Chemical formula 4]

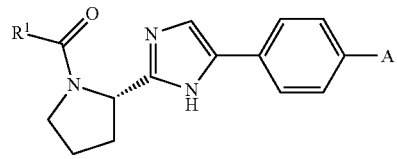

In the Chemical formula 4,
$R^1$ is $C_1$-$C_6$ alkyl, $C_1$-$C_6$ alkoxy or —$CH(R^3)NHCO_2R^4$,
$R^3$ is $C_1$-$C_6$ alkyl or $C_6$-$C_{10}$ aryl,
$R^4$ is $C_1$-$C_6$ alkyl, and
A is a halogen including iodo or brome, bronic acid [$B(OH)_2$], $C_1$-$C_6$ alkyl or pinacol borate,

[Chemical formula 5]

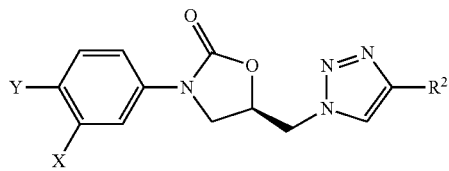

In the Chemical formula 5,
$R^2$ is H, $(CH_2)_n WR^5$ or $C_6$-$C_{10}$ aryl, n is an integer of 0 or 1 to 4,
$R^5$ is H, $C_1$-$C_6$ alkyl, benzyl, or $C_1$-$C_6$ alkyl carbonyl,
X is H or F,
W is oxygen or nitrogen, and
Y is halogen such as iodo or brome, bronic acid [B(OH)$_2$], $C_1$-$C_6$ alkyl or bronic acid pinacol ester.

[Chemical formula 7]

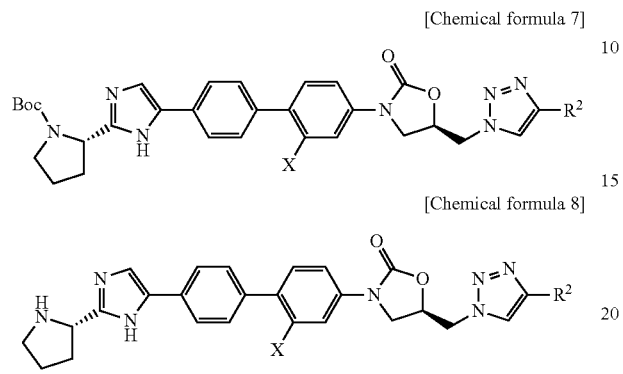

[Chemical formula 8]

In the Chemical formula 7 and Chemical formula 8,
$R^2$ is H, (CH$_2$)$_n$WR$^5$ or $C_6$-$C_{10}$ aryl
n is an integer of 0 or 1 to 4,
$R^5$ is H, $C_1$-$C_6$ alkyl, benzyl, or $C_1$-$C_6$ alkyl carbonyl,
W is oxygen or nitrogen, and
X is H or F.

In step (1), the standard Suzuki binding reaction can be performed according to the Reaction scheme I, by using the compound of Chemical formula 4 and the compound of Chemical formula 5.

Among the compounds of Chemical Formula 4, the compound of Chemical formula 4-1 having a protection group of N-Boc is shown below, and can be prepared according to the methods disclosed in WO 2010096777 (A=Br), WO 2010148006 (A=I), and WO 2010096462 (A=pinacole boric acid ester)]:

[Chemical formula 4-1]

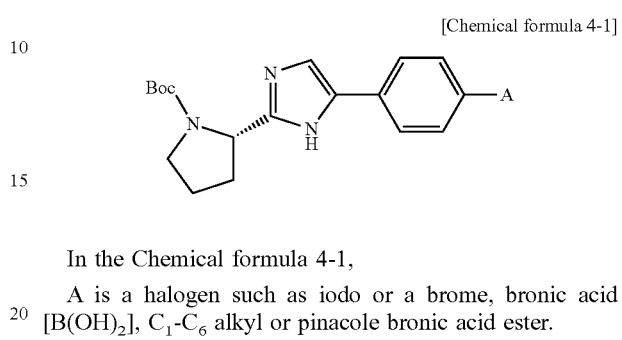

In the Chemical formula 4-1,
A is a halogen such as iodo or a brome, bronic acid [B(OH)$_2$], $C_1$-$C_6$ alkyl or pinacole bronic acid ester.

The compound of Chemical formula of can be prepared by referring to the disclosures of WO 2005116022 (Y=B(OH)$_2$), T. Komine et al. *J. Med. Chem.*, 2008, 51, 6558 (Y=pinacole boric acid ester), WO 2003035648, F. Reck et al. *J. Med. Chem*, 2007, 50, 4868 (Y=I), and WO 2004048350 ($R^2$=CH$_2$OH, Y=I).

The compounds of Chemical formula 5-1 where Y is iodo in the compounds of Chemical formula 5, can be prepared from the compound of Chemical formula 6, according to the method of Reaction scheme 2.

[Reaction scheme 1]

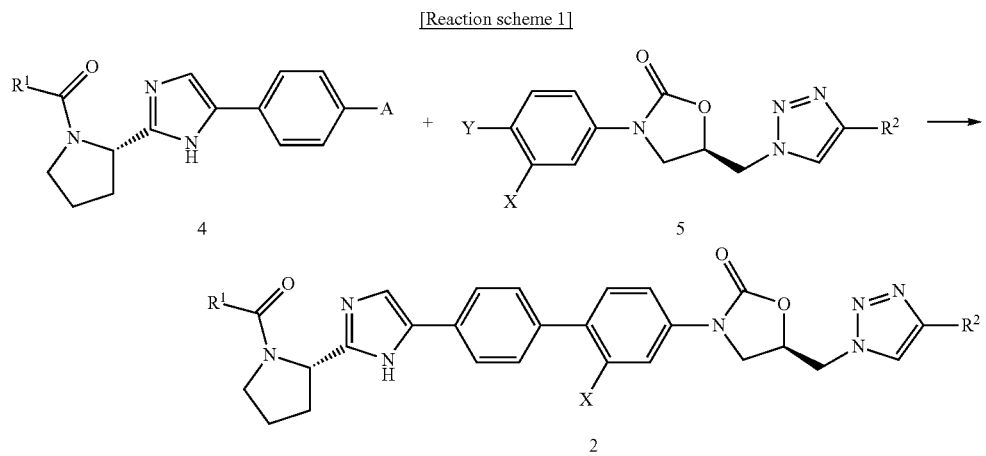

In the preparation method shown in Reaction scheme 1, the compound of Chemical formula 2 can be prepared from the compound of Chemical formula 4 and the compound of Chemical formula 5, according to the standard Suzuki binding reaction using Pd-based catalyst [N. Miyaura & A. Suzuki, Palladium-Catalyzed Cross-Coupling Reactions of Organoboron Compounds, Chemical Reviews 95 (7): 2457-2483 (1995)].

The preparation method of the compound represented by Chemical formula 4 can be referred to the disclosures of the references of WO 2010148006, WO 2010099527 and WO 2010132538.

[Reaction scheme 2]

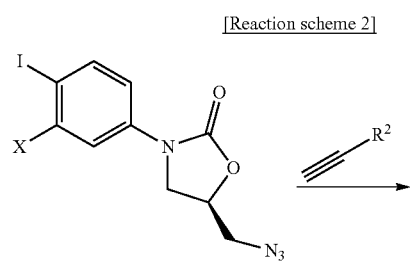

-continued

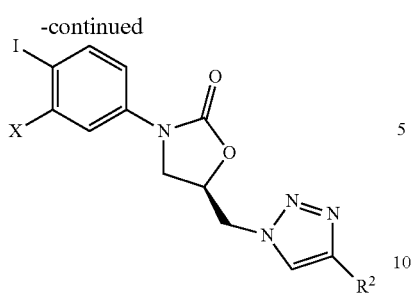

CuI, CH₃CN, or CuSO₄, sodium ascorbate, t-BuOH, H₂O, rt, 1 h

[Chemical formula 5-1]

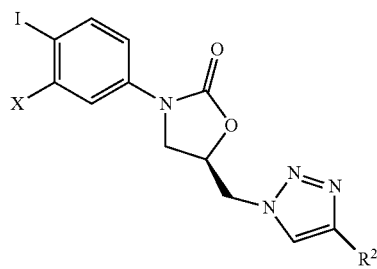

In the Chemical formula 5-1,
$R^2$ is H, $(CH_2)_n WR^5$ or $C_6$-$C_{10}$ aryl,
n is an integer of 0 to 4,
$R^5$ is H, $C_1$-$C_6$ alkyl, benzyl, or $C_1$-$C_6$ alkyl carbonyl,
X si H or F, and
W is oxygen or nitrogen.

[Chemical formula 6]

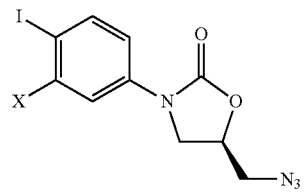

In the Chemical formula 6, X is H or F.

The compound of Chemical formula 6 can be prepared by using the method disclosed in the references such as WO 2003022824 or F. Reck, et al. *J. Med. Chem.* 2007, 50, 4868.

According to the method of Reaction scheme 3, the compound of Chemical Formula 2 can be prepared by using the compound of Chemical formula 4-1 and the compound of Chemical formula 5 through the standard Suzuki reaction to produce the N-Boc-protected the compound of Chemical formula 7; deprotecting Boc protecting group to obtain the amine compound of Chemical formula 8; and then reacting with a carboxylic acid derivative through the standard amide binding (S.-Y. Han, Y.-A. Kim, *Tetrahedron*, 2004, 60, 2447).

[Reaction scheme 3]

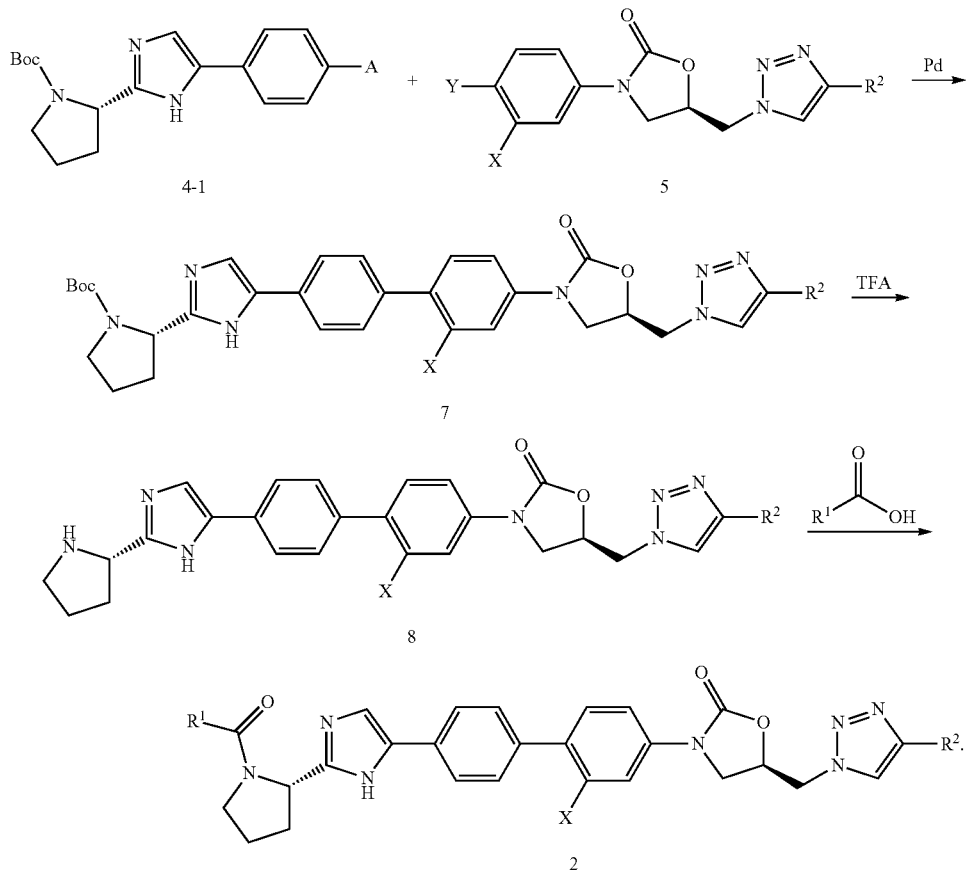

[Chemical formula 7]

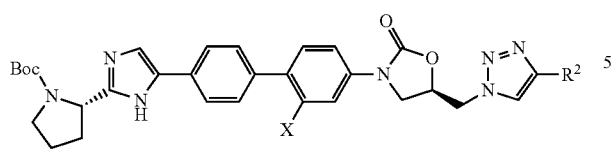

[Chemical formula 8]

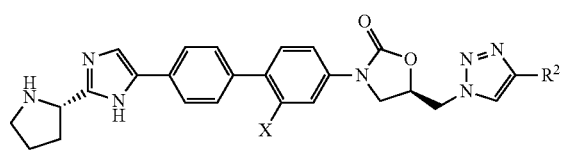

In the Chemical formula 7 and Chemical formula 8, $R^2$ is H, $(CH_2)_n WR^5$ or $C_6$-$C_{10}$ aryl n is an integer of 0 to 4, W is oxygen or nitrogen, $R^5$ is H, $C_1$-$C_6$ alkyl, benzyl, or $C_1$-$C_6$ alkyl carbonyl, and X is H or F.

Preparation Method 2

Oxazolidinone Compounds of Chemical Formula 3

As illustrated below, the method of preparing the compounds of Chemical formula 3, pharmaceutically acceptable salt thereof or hydrate includes a step of binding the compound of Chemical formula 4 with the compound of Chemical formula 9.

Specifically, the method of preparing the compounds of Chemical formula 3 includes:

(1) reacting the compound of Chemical formula 4 and the compounds of Chemical formula 9 according to the standard Suzuki reaction, to produce the compound of Chemical Formula 10;

(2) de-protecting Boc group of the compound represented by Chemical Formula 10 to produce the compound of Chemical Formula 11; and (3) reacting the compound of Chemical Formula 11 with carboxylic acid derivative via the standard amide binding method to produce the compound of Chemical formula 3.

[Chemical formula 3]

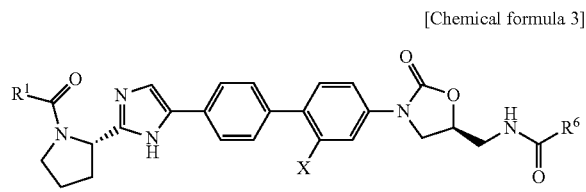

In the Chemical formula 3, $R^1$ and $R^6$ is independently $C_1$-$C_6$ alkyl, $C_1$-$C_6$ alkoxy or —$CH(R^3)NHCO_2R^4$, $R^3$ is $C_1$-$C_6$ alkyl or $C_6$-$C_{10}$ aryl, $R^4$ is $C_1$-$C_6$ alkyl, and X is H or F.

[Chemical formula 4]

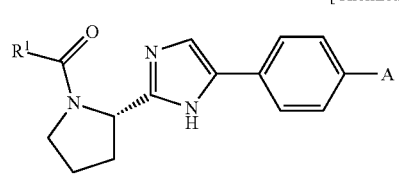

In the Chemical formula 4, $R^1$ is $C_1$-$C_6$ alkyl, $C_1$-$C_6$ alkoxy or —$CH(R^3)NHCO_2R^4$, $R^3$ is $C_1$-$C_6$ alkyl or $C_6$-$C_{10}$ aryl, $R^4$ is $C_1$-$C_6$ alkyl, and A is halogen such as iodo or brome, bronic acid [$B(OH)_2$], $C_1$-$C_6$ alkyl or pinacol borate.

[Chemical formula 9]

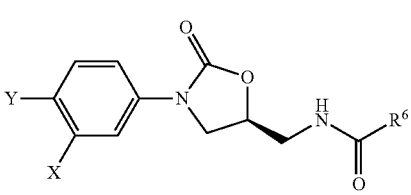

In the Chemical formula 9, $R^6$ is $C_1$-$C_6$ alkyl, $C_1$-$C_6$ alkoxy or —$CH(R^3)NHCO_2R^4$, $R^3$ is $C_1$-$C_6$ alkyl or $C_6$-$C_{10}$ aryl, $R^4$ is $C_1$-$C_6$ alkyl, X is H or F, and Y is halogen such as iodo or brome, bronic acid [$B(OH)_2$], $C_1$-$C_6$ alkyl or pinacol borate.

[Chemical Formula 10]

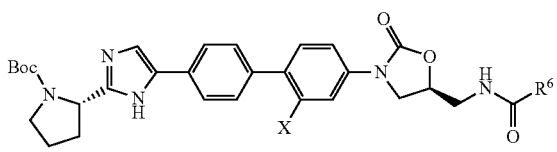

[Chemical Formula 11]

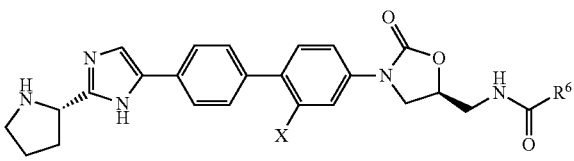

In the chemical Formula 10 and 11, $R^6$ is $C_1$-$C_6$ alkyl, $C_1$-$C_6$ alkoxy or —$CH(R^3)NHCO_2R^4$, $R^3$ is $C_1$-$C_6$ alkyl or $C_6$-$C_{10}$ aryl, $R^4$ is $C_1$-$C_6$ alkyl, and X is H or F.

In step (1), the Suzuki reaction of the compound of Chemical formula 4 and the compound of Chemical formula 9 can be performed according to the Reaction scheme 4.

[Reaction scheme 4]

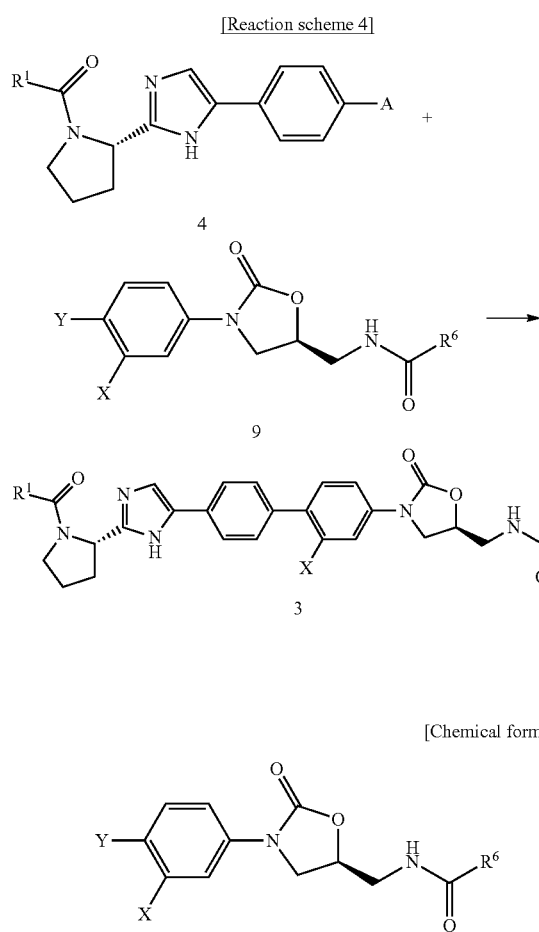

In the Reaction scheme 5 which modifies the Reaction scheme 3, the method of preparing the compounds of Chemical formula 3, pharmaceutically acceptable salt thereof or hydrate can be prepared by using the steps of binding the compound of Chemical formula 4-1 with the compound of Chemical formula 9 according to the standard Suzuki reaction, to produce the compound of Chemical Formula 10 including a protecting group of N-Boc, deprotecting Boc group of the compound represented by Chemical Formula 10 to produce the compound of Chemical Formula 11; and reacting the compound of Chemical Formula 11 with carboxylic acid derivative via the standard amide binding method.

[Reaction scheme 5]

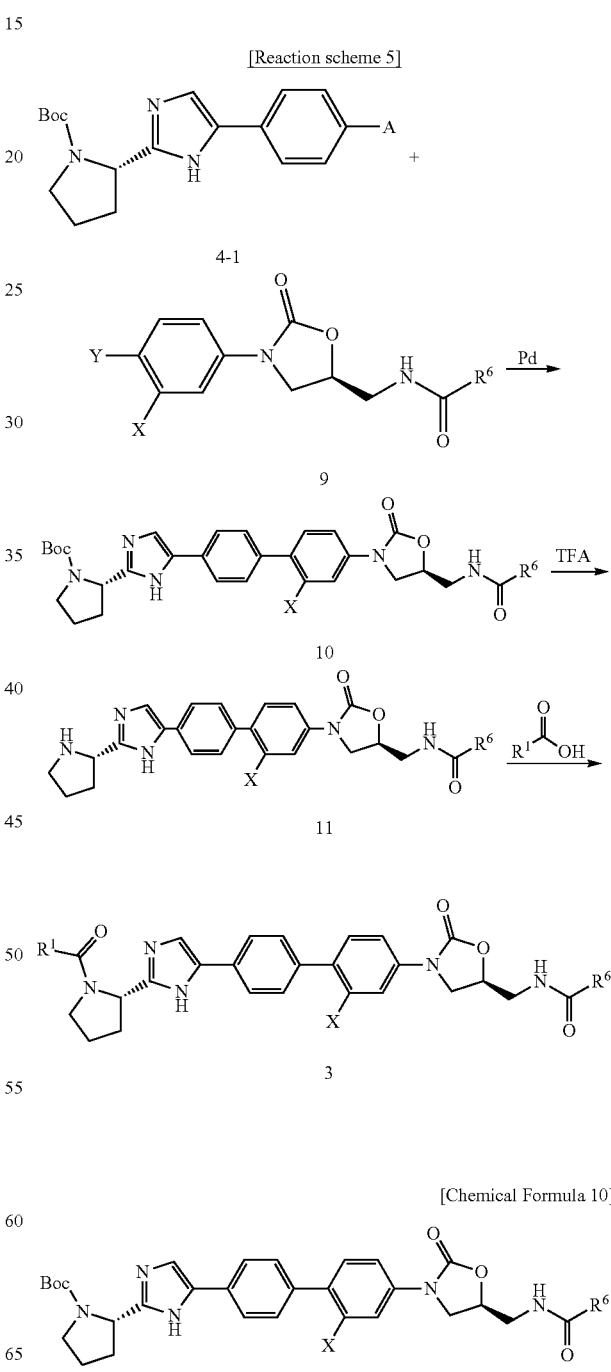

[Chemical formula 9]

In the Chemical formula 9,
$R^6$ is $C_1$-$C_6$ alkyl, $C_1$-$C_6$ alkoxy or —CH($R^3$)NHCO$_2$R$^4$,
$R^3$ is $C_1$-$C_6$ alkyl or $C_6$-$C_{10}$ aryl,
$R^4$ is $C_1$-$C_6$ alkyl,
X is H or F, and
Y is halogen such as iodo or brome, bronic acid [B(OH)$_2$], $C_1$-$C_6$ alkyl or pinacol borate.

The production of the compound of Chemical formula 9-1 where $R^6$ is a methyl in the Chemical formula 9 can be prepared by referring to the disclosures of WO 2001094342 (Y=I) and WO 2004056817 (Y=pinacol borate). The other compound of Chemical formula 9 can be prepared by modifying the production method of Chemical formula 9-1, for example a method known in the prior art.

[Chemical formula 9-1]

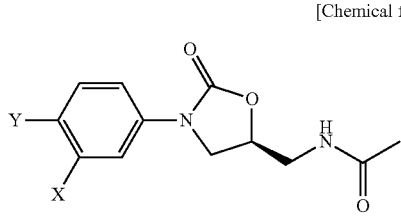

In the Chemical formula 9-1,
X is H or F, and
Y is halogen such as iodo or brome, bronic acid [B(OH)$_2$], $C_1$-$C_6$ alkyl or pinacol borate.

In the Chemical Formula 10
R⁶ is $C_1$-$C_6$ alkyl, $C_1$-$C_6$ alkoxy or —CH(R³)NHCO₂R⁴,
R³ is $C_1$-$C_6$ alkyl or $C_6$-$C_{10}$ aryl,
R⁴ is $C_1$-$C_6$ alkyl, and
X is H or F.

[Chemical Formula 11]

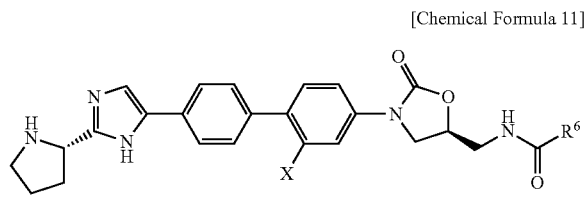

In the Chemical Formula 11,
R⁶ is $C_1$-$C_6$ alkyl, $C_1$-$C_6$ alkoxy or —CH(R³)NHCO₂R⁴,
R³ is $C_1$-$C_6$ alkyl or $C_6$-$C_{10}$ aryl,
R⁴ is $C_1$-$C_6$ alkyl, and
X is H or F.

The oxazolidinone compounds represented by Chemical Formula 1, preferably Chemical Formula 2 or Chemical formula 3, pharmaceutically acceptable salts thereof or hydrates show a low cytotoxicity with excellent inhibitory activity on the growth and activity of HCV (Experimental Example 1 and 2), thereby can be applied to anti-viral agent, or an agent for preventing or treating diseases related with HCV infection.

Another embodiment is to provide a pharmaceutical composition for preventing or treating a disease related with HCV, including the oxazolidinone compounds represented by Chemical Formula 1, preferably Chemical Formula 2 or Chemical formula 3, pharmaceutically acceptable salts thereof or hydrates as an effective agent, or an anti-viral composition for HCV.

The pharmaceutical composition or the anti-viral composition model animals such as mouse, rat, rabbit, Guinea pig and hamster, but not limited thereto, preferably primates such as human, more preferably human.

An embodiment of the present invention relates to a method of preventing or treating a disease related with Hepatitis C virus (HCV) infection, comprising administering the oxazolidinone compound, pharmaceutically acceptable salt thereof, or hydrate, to a subject in need.

An embodiment of the present invention relates to a method of inhibiting a growth or an activity of HCV, comprising a step of treating an oxazolidinone compound, pharmaceutically acceptable salt thereof, or hydrate, at an anti-virally effective amount.

The pharmaceutically acceptable salt of oxazolidinone compound can be a salt of organic acid or inorganic acid selected from the group consisting of a hydrochloric acid, a hydrobromic acid, a sulfuric acid, a phosphoric acid, nitric acid, acetic acid, glycolic acid, lactic acid, pyruvic acid, malonic acid, succinic acid, glutaric acid, fumaric acid, malic acid, a mandelic acid, tartaric acid, citric acid, ascorbic acid, palmitic acid, maleic acid, hydroxymaleic acid, benzoic acid, hydroxybenzoic acid, phenylacetic acid, cinnamic acid, salicylic acid, methanesulfonic acid, benzene sulfonic acid and toluene sulfonic acid.

The used amount of the oxazolidinone compound represented by Chemical Formula 1, preferably Chemical Formula 2 or Chemical formula 3, pharmaceutically acceptable salts thereof or hydrates can be adjusted depending on the administering mode or method of pharmaceutical composition by an ordinarily-skilled person in the art.

Preferably, the oxazolidinone compound represented by Chemical Formula 1, preferably Chemical Formula 2 or Chemical formula 3, pharmaceutically acceptable salts thereof or hydrates can be used at an amount of 0.5 to 10 wt % based on the total amount of composition.

The oxazolidinone compounds represented by Chemical Formula 1, preferably Chemical Formula 2 or Chemical formula 3, pharmaceutically acceptable salts thereof or hydrates can be used as a single component in the pharmaceutical composition or the anti-viral composition, or together with a pharmaceutically-acceptable carriers, excipient, diluent, or auxiliary components.

The examples of carriers, excipient and diluent can include at least one selected from the group consisting of lactose, dextrose, sucrose, sorbitol, mannitol, xylitol, erythritol, maltitol, starch, acacia gum, alginate, gelatin, calcium phosphate, calcium silicate, cellulose, methylcellulose, microcrystal cellulose, polyvinyl pyrrolidone, water, methylhydroxybenzoate, propylhydroxybenzoate, talc, magnesium stearate and mineral oils, propylhydroxybenzoate, dextrin, calcium carbonate, propyl glycol, liquid paraffin and saline, but not limited thereto.

The pharmaceutical composition can further include filler, thickening agent, binding agent, disintegrating agent, anticoagulating agent, lubricant, wetting agent, pH adjusting agent, nutrient, vitamin, electrolyte, alginate and its salt, pectic acid and its salt, protective colloid, glycerin, fragrant, surfactant, or preservative.

Besides an effective agent, the pharmaceutical composition or the anti-viral composition can further include at least known other anti-viral agent or other drugs, and can be administered simultaneously or sequentially as a combination therapy. The additional other anti-viral agent or other drugs can be Interferon, a combination of Interferon-Ribavirin, or at least one selected from the group consisting of the agents of inhibiting HCV protease, NS5A, HCV polymerase or HCV serine protease, The anti-viral agent can include a therapeutic vaccine or DNA.

The administration method of the pharmaceutical composition or the anti-viral composition can include oral or paraenteral method, for examples, various routs such as oral, transdermal, subcutaneous, intravenous and intramuscular. In addition, the formulation of composition can be any one prepared according any method known in the art, in order that the effective ingredient can be released fast, slow or in delayed mode after administration. Generally, the solid formulation for oral administration can include tablet, pill, soft capsule, hard capsule, powder and granule, and can include at least excipient, for example starch, calcium carbonate, sucrose, lactose, or gelatin. Besides the simple excipients, a lubricant such as magnesium stearate and talc can be used. The liquid formulation for oral administration can be suspension, solution, emulsion, syrup and the like, and include various excipients such as wetting agent, sweetening agent, perfume, preservative and the like, as well as simple diluents such as water and liquid paraffin. The paraenteral formulation can be cream, lotion, ointment, plaster, liquids and soultion, aerosol, fruidextract, elixir, infusion, sachet, patch or injections. The injectable formation can be preferably isotonic aqueous solution or suspension.

The pharmaceutical composition or the anti-viral composition can further auxiliary agents such as sterilizing agent, preservative, stabilizing agent, hydrating agent, emulsifying agent, osmotic salt and buffering agent, and other therapeutically-effective components, can be formulated as mixing, granulating, or coating method, or other well-known formulation method.

In addition, the administering amount of pharmaceutical composition or the anti-viral composition can be determined by considering the administering method, the age and gender of a subject, disease severity, disease state, absorbing degree of active ingredient in body, inactive rate and a drug used in combination therapy, and can be administered once or several times.

As an effective ingredient in the administering amount of pharmaceutical composition or the anti-viral composition, the oxazolidinone compounds represented by Chemical Formula 1, preferably Chemical Formula 2 or Chemical formula 3, pharmaceutically acceptable salts thereof or hydrates can be administered to a mammal such as human at an amount of 0.001 to 100 mg/kg (body weight) per a day, or preferably 0.01 to 35 mg/kg, at one time or several times by oral or paraenteral route.

Another embodiment of the present invention is to provide a method of preventing or treating HCV infection, comprising administering the anti-viral composition for HCV at a therapeutically-effective amount to a subject in need.

Preferably, the method may include a method of preventing or treating a cell infected with HCV. The infected cell includes any cell infected with HCV, for example prokaryotic cell, eukaryotic cell, immortalized cell, primary cell lines, bacterial culture and in situ cell.

Preferably, the method can further include a step of identifying a subject needed for the prevention or treatment of HCV infection.

The subject to be applied by the method is the same described above in the pharmaceutical composition or the anti-viral composition.

Hereinafter, the term, "therapeutically-effective amount" means an amount used for alleviating and/or treating HCV infection in a mammal, and can be determined by considering the disease kind, disease severity, effective ingredient in the composition, kind and amount of other components, formulation type, age, bodyweight, condition and gender of patient, diet, administration time, administration route, half-life of composition, the administration period, and other drugs in the combination therapy. For example, the therapeutically-effective amount can be 0.001 to 100 mg/kg body weight/day or preferably 0.01 to 35 mg/kg body weight/day once or several times in a day, by oral or paraenteral route.

The composition for preventing or treating a disease related with Hepatitis C virus (HCV) infection, comprising administering the oxazolidinone compounds, pharmaceutically acceptable salt thereof, or hydrate, shows a low cytotoxicity with an excellent inhibitory activity of HCV growth or activity of HCV, and thus can be useful for anti-viral agent or a pharmaceutical composition for preventing or treating a disease related with Hepatitis C virus (HCV) infection.

The present invention is further explained in more detail with reference to the following examples. These examples, however, should not be interpreted as limiting the scope of the present invention in any manner.

EXAMPLE

Preparation of Oxazolidinone Compounds

Example 1 tert-butyl (S)-2-(5-(4'-((R)-5-((1H-1,2,3-triazole-1-yl)methyl)-2-oxooxazolidin-3-yl)-2'-fluoro-[1,1'-biphenyl]-4-yl)-1H-imidazole-2-yl)pyrrolidine-1-carboxylate[tert-Butyl(S)-2-(5-(4'-((R)-5-((1H-1,2,3-triazol-1-yl)methyl)-2-oxooxazolidin-3-yl)-2'-fluoro-[1,1'-biphenyl]-4-yl)-1H-imidazol-2-yl)pyrrolidine-1-carboxylate]

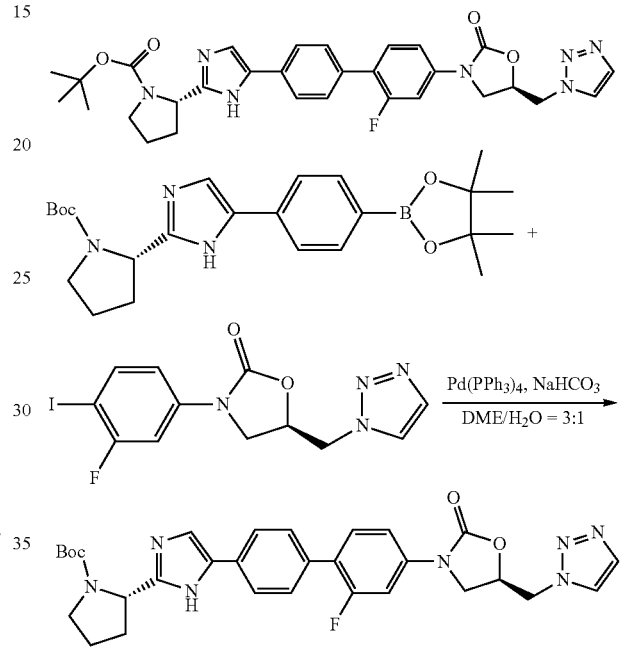

In Ar atmosphere, tert-butyl (S)-2-(5-(4-(4,4,5,5-tetramethyl-1,3,2-dioxaborolan-2-yl)phenyl)-1H-imidazol-2-yl)pyrrolidine-1-carboxylate (60 mg, 0.14 mmol) (WO 2010096462) was dissolved in a solvent (3 mL, DME:H$_2$O=3:1) under Ar atmosphere and was added with (R)-5-((1H-1,2,3-triazol-1-yl)methyl)-3-(3-fluoro-4-iodophenyl)oxazolidin-2-one (48 mg, 0.12 mmol) (WO 2003035648 and F. Reck et al. *J. Med. Chem*, 2007, 50, 4868), and NaHCO$_3$ (32 mg, 0.39 mmol), tetrakis(triphenylphosphine)palladium [Pd(PPh$_3$)$_4$, 7.9 mg, 0.0068 mmol, 5 mol %]. The obtained mixture was agitated at 85° C. for about 24 hours and the reaction termination was confirmed by TLC (MC:MeOH:H$_2$O:NH$_4$OH=280:20:1:1). The reaction solution was cooled to a room temperature, added by dichloromethane (DCM, 5 mL), and then washed with H$_2$O (5 mL). The aqueous layer was extracted with DCM (5 mL) and the organic layer was collected. The collected organic layer was dried with Na$_2$SO$_4$, filtered and concentrated with vacuum evaporation. The concentrated solution was purified by using column chromatograph (MC:MeOH:H$_2$O:NH$_4$OH=480:20:1:1), to obtain the subject compound (41 mg, 55% yield).

$^1$H NMR (400 MHz, DMSO): δ 8.19 (s, 1H), 7.84 (d, J=8.0 Hz, 2H), 7.82 (s, 1H), 7.56 (m, 5H), 7.34 (m, 2H), 5.17 (m, 1H), 4.86 (d, J=4.8 Hz, 2H), 4.29 (t, J=9.2 Hz, 1H), 4.19 (d, J=5.4 Hz, 2H), 3.94 (m, 1H), 1.40 (s, 9H); $^{13}$C NMR (75 MHz, DMSO): δ171.55, 161.37, 158.09, 156.27, 154.41, 134.39, 134.26, 130.88, 130.71, 130.63, 129.98, 124.83, 113.56, 106.48, 106.09, 80.35, 72.09, 54.34, 47.46, 47.32, 41.80, 29.00, 29.00, 28.51, 24.76, 28.51, 24.76, 23.00.

Example 2
(R)-5-((1H-1,2,3-triazole-1-yl)methyl)-3-(4'-(2-((S)-1-acetylpyrrolidine-2-yl)-1H-imidazole-5-yl)-2-fluoro-[1,1'-biphenyl]-4-yl)oxazolidine-2- [(R)-5-((1H-1,2,3-Triazol-1-yl)methyl)-3-(4'-(2-((S)-1-acetylpyrrolidin-2-yl)-1H-imidazol-5-yl)-2-fluoro-[1,1'-biphenyl]-4-yl)oxazolidin-2-one]
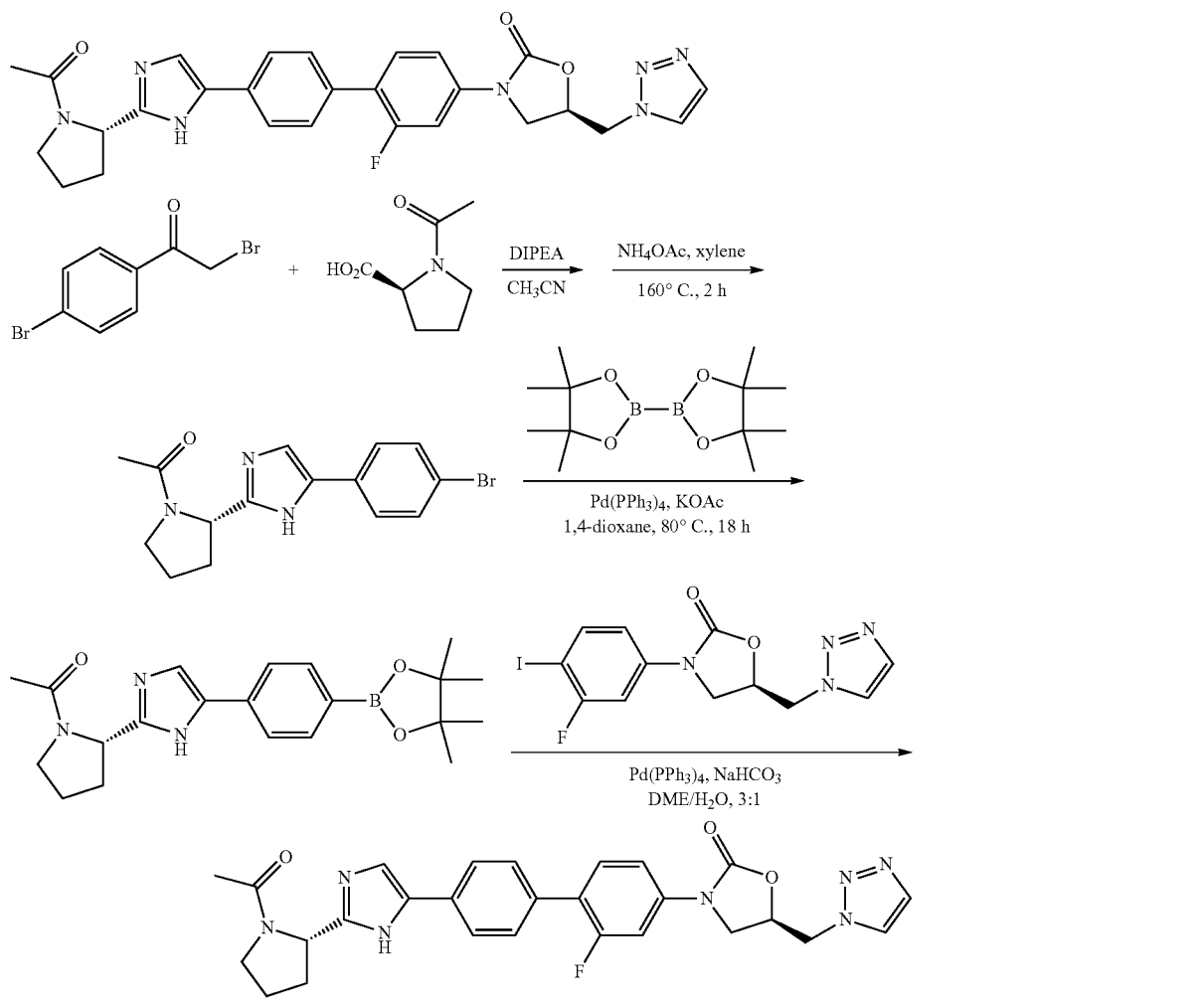
Step (1). (S)-1-(2-(5-(4-Bromophenyl)-1H-imidazol-2-yl)pyrrolidin-1-yl)ethanone
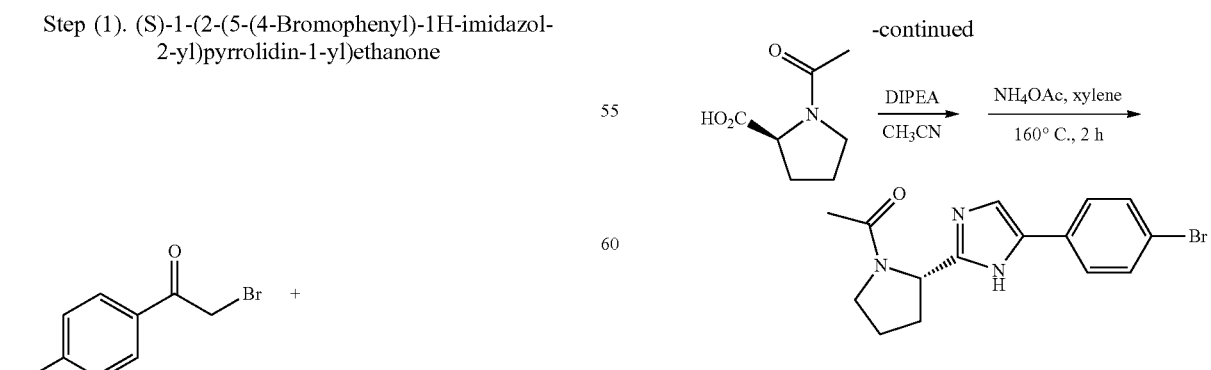
In Ar atmosphere, 2-bromo-1-(4-bromophenyl)ethanone (2 g, 7.2 mmol) was dissolved in acetonitrile (18 ml) under Ar atmosphere, added with (S)-1-acetylpyrrolidine-2-carboxylic acid (1.1 g, 7.2 mmol) and DIPEA (1.4 g, 10.8 mmol) at 0° C., and agitated at a room temperature for 4 hours. The reaction termination was confirmed by TLC (Hex:EA=2:1) and performed by vacuum evaporation to remove the solvent. The concentrated solution was added with ethylacetate (20 mL) and washed with H$_2$O. The aqueous layer was extracted with ethylacetate (10 mL) and the organic layer was dried with Na$_2$SO$_4$, filtered and concentrated with vacuum evaporation. The product was transferred to a pressure tube, dissolved in xylene (20 mL) and agitated at 160° C. for 2 hours with addition of NH$_4$OAc (2.8 g, 10.8 mmol). The reaction termination was confirmed by TLC (HX:EA=1:1), cooled to a room temperature and concentrated with vacuum evaporation. The concentrated solution was added with dichloromethane (DCM, 20 mL) and washed with H$_2$O (10 mL). The aqueous layer was extracted with DCM (10 mL), and the organic layer was collected. The collected organic layer was dried with Na$_2$SO$_4$, filter and concentrated. The concentrated solution was purified with column chromatograph(Hex/EA=1:1), to obtain the subject compound (1.93 g. 80%).

$^1$H NMR (300 MHz, CDCl$_3$): δ9.81 (s, 1H), 7.53 (m, 2H), 7.27 (m, 1H), 7.20 (m, 1H), 5.21 (d, J=6.3 Hz, 1H), 3.55 (m, 2H), 2.96 (s, 3H), 2.31 (m, 2H), 2.09 (m, 4H); $^{13}$C-NMR (75 MHz, CDCl$_3$): δ174.66, δ171.43, δ148.66, 131.68, 126.49, 126.27, 120.22, 54.16, 48.61, 27.92, 25.26, 422.74, 21.14

Step (2). (S)-1-(2-(5-(4-(4,4,5,5-tetramethyl-1,3,2-dioxaborolan-2-yl)phenyl)-1H-imidazol-2-yl)pyrrolidin-1-yl)ethanone

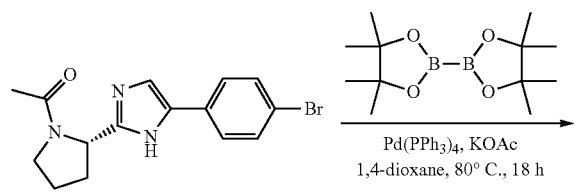

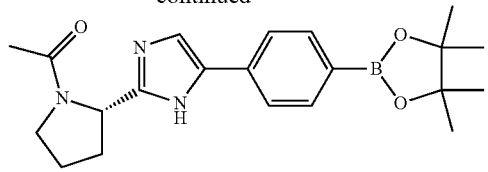

In Ar atmosphere, (S)-1-(2-(5-(4-bromophenyl)-1H-imidazol-2-yl)pyrrolidin-1-yl)ethanone (140 mg, 0.41 mmol) obtained in Step (1) was dissolved in 1.4-Dioxane (2 ml), added with bis(pinacolato)diboron (210 mg, 0.82 mmol), potassium acetate (101 mg, 1.03 mmol), and tetrakis(triphenylphosphine)palladium (18 mg, 0.016 mmol), and agitated at 85° C. for 24 hours. The reacting solution was concentrated, added with ethyl acetate (20 mL) and then washed with H$_2$O. The aqueous solution was extracted with ethylacetate (10 mL), and the organic layer was collected. The collected organic layer was dried with Na$_2$SO$_4$, filter and concentrated under vacuum. The concentrated solution was purified with column chromatography (MC:MeOH:H$_2$O: NH$_4$OH=380:20:1:1), to obtain the subject compound (140 mg, 90% yield).

$^1$H NMR (300 MHz, DMSO): δ7.97 (br s, 1H), 7.67 (m, 2H), 7.63 (m, 2H), 7.63 (m, 3H), 5.07 (m, 2H), 3.47 (m, 3H), 2.07 (m, 7H), 1.29 (s, 12H).

Step (3). (R)-5-((1H-1,2,3-triazol-1-yl)methyl)-3-(4'-(2-((S)-1-acetyl pyrrolidin-2-yl)-1H-imidazol-5-yl)-2-fluoro-[1,1'-biphenyl]-4-yl)oxazolidin-2-one

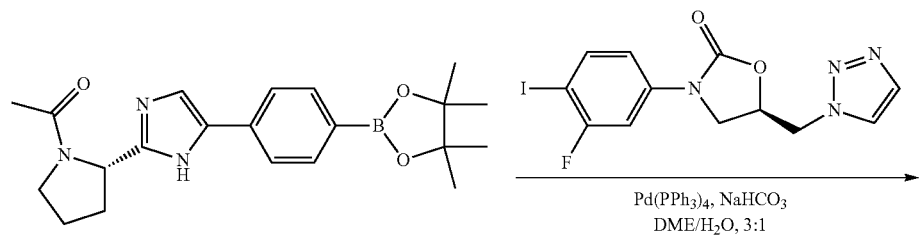

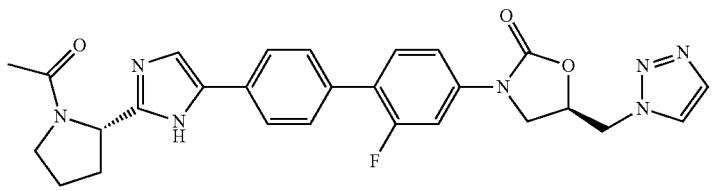

The subject compound (22 mg, 16%) was obtained from (S)-1-(2-(5-(4-(4,4,5,5-tetramethyl-1,3,2-dioxaborolan-2-yl)phenyl)-1H-imidazol-2-yl) pyrrolidin-1-yl)ethanone (100 mg, 0.26 mmol) and (R)-5-((1H-1,2,3-triazol-1-yl)methyl)-3-(3-fluoro-4-iodophenyl)oxazolidin-2-one, according to the same method of Example 1.

$^1$H NMR (400 MHz, DMSO): δ11.76 (s, 1H), 8.20 (s, 1H), 7.85 (m, 2H), 7.91 (s, 1H), 7.58 (m, 5H), 7.38 (dd, J=8.6, 1.8 Hz, 1H), 5.18 (m, 1H), 5.08 (m, 1H), 4.88 (d, J=4.8 Hz, 2H), 4.31 (t, J=9.2 Hz, 1H), 3.97 (dd, J=9.4, 5.8 Hz, 1H), 4.31 (t, J=9.2 Hz, 1H), 3.97 (dd, J=9.4, 5.8 Hz, 1H), 3.70 (m, 1H), 2.52 (m, 1H), 2.14 (m, 7H); $^{13}$C NMR (75 MHz, DMSO): δ171.30, 160.97, 158.51, 153.21, 148.81, 137.68, 137.58, 134.49, 133.05, 130.74, 130.69, 129.04, 125.08, 124.72, 113.76, 113.73, 106.70, 106.41, 70.52, 54.20, 52.00, 48.60, 47.21, 34.57, 30.90, 27.85, 25.26, 22.74, 22.47.

Example 3 methyl ((S)-1-((S)-2-(5-(4'-((R)-5-((1H-1,2,3-triazole-1-yl)methyl)-2-oxoxazolidin-3-yl)-2'-fluoro-[1,1'-biphenyl]-4-yl)-1H-imidazole-2-yl)pyrrolidine-1-yl)-3-methyl-1-oxobutane-2-yl)carbamate[Methyl ((S)-1-((S)-2-(5-(4'-((R)-5-((1H-1,2,3-triazol-1-yl)methyl)-2-oxooxazolidin-3-yl)-2'-fluoro-[1,1'-biphenyl]-4-yl)-1H-imidazol-2-yl)pyrrolidin-1-yl)-3-methyl-1-oxobutan-2-yl)carbamate]

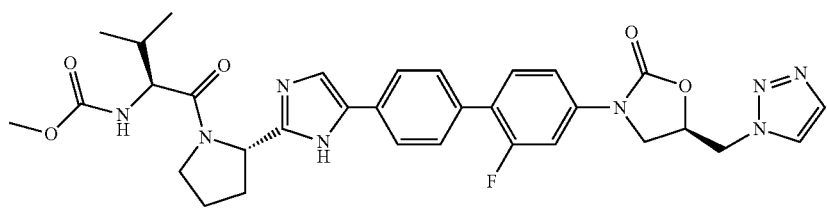

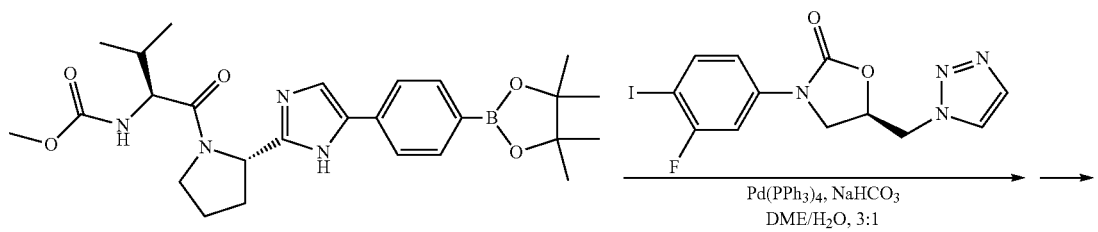

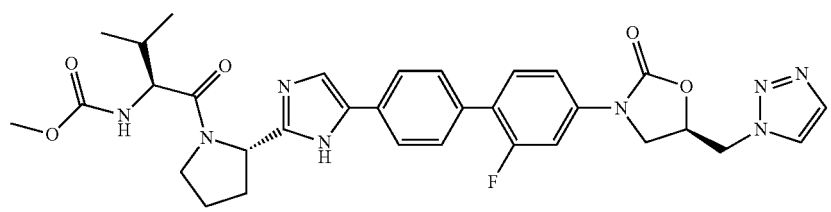

The subject compound (24 mg, 39%) was obtained from methyl ((S)-3-methyl-1-oxo-1-((S)-2-(5-(4-(4,4,5,5-tetramethyl-1,3,2-dioxaborolan-2-yl)phenyl)-1H-imidazol-2-yl)pyrrolidin-1-yl)butan-2-yl)carbamate (WO 2010148006, 50 mg, 0.10 mmol) and (R)-5-((1H-1,2,3-triazol-1-yl)methyl)-3-(3-fluoro-4-iodophenyl)oxazolidin-2-one, according to the same method of Example 1.

$^1$H-NMR (400 MHz, DMSO): δ 11.93 (br s, 1H), 8.45 (br s, 1H), 8.20 (d, J=0.8 Hz, 1H), 7.83 (m, 2H), 7.79 (d, J=0.8 Hz, 1H), 7.61 (t, J=9.0 Hz, 2H), 7.54 (m, 3H), 7.37 (dd, J=8.8, 2.0 Hz, 1H), 5.18 (m, 1H), 4.87 (d, J=5.2 Hz, 1H), 4.33 (m, 3H), 3.96 (dd, J=7.2, 3.0, 1H), 3.90 (m, 1H), 3.56 (s, 3H), 1.27 (m, 1H), 0.87 (t, 6H); $^{13}$C NMR (100 MHz, CDCl$_3$): δ 170.86, 160.63, 158.21, 157.27, 153.81, 149.81, 193.16, 134.95, 133.88, 131.08, 129.00, 126.35, 124.74, 114.55, 106.30, 106.01, 71.46, 58.46, 54.68, 52.19, 51.89, 47.47, 47.28, 31.42, 30.30, 25.42, 24.71, 22.52, 19.42, 18.97, 14.42.

Example 4 methyl ((S)-2-((S)-2-(5-(4'-((R)-5-((1H-1,2,3-triazole-1-yl)methyl)-2-oxoxazolidin-3-yl)-2'-fluoro-[1,1'-biphenyl]-4-yl)-1H-imidazole-2-yl)pyrrolidine-1-yl)-2-oxo-1-phenylethyl)carbamate[methyl ((S)-2-((S)-2-(5-(4'-((R)-5-((1H-1,2,3-triazol-1-yl)methyl)-2-oxooxazolidin-3-yl)-2'-fluoro-[1,1'-biphenyl]-4-yl)-1H-imidazol-2-yl)pyrrolidin-1-yl)-2-oxo-1-phenylethyl)carbamate]

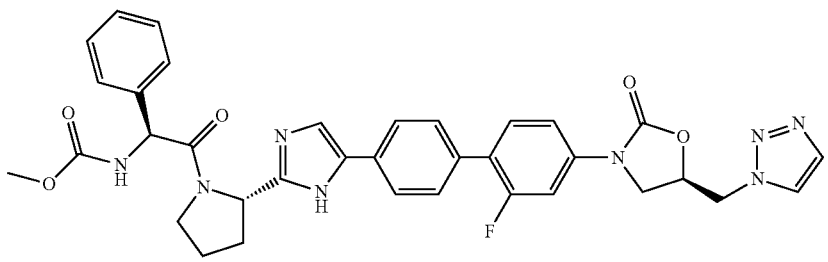

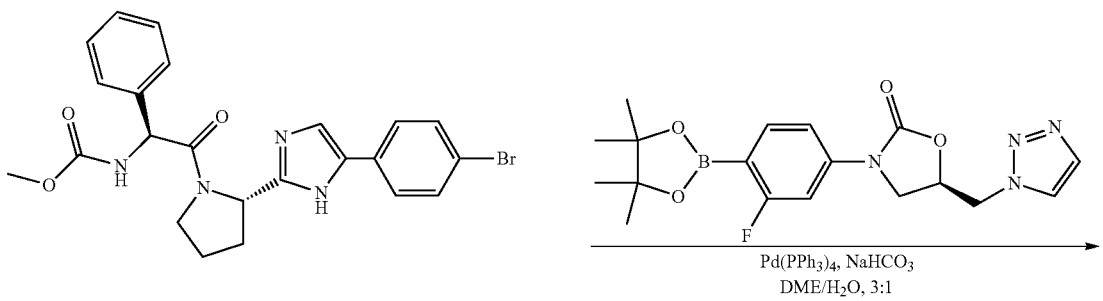

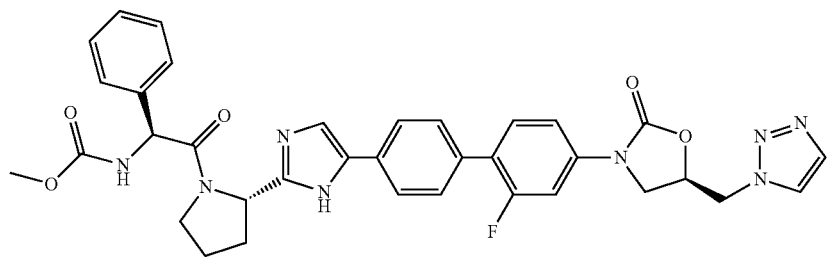

The subject compound (32.9 mg, 0.05 mmol) was obtained from methyl((S)-2-((S)-2-(5-(4-bromophenyl)-1H-imidazol-2-yl)pyrrolidin-1-yl)-2-oxo-1-phenylethyl)carbamate (53.7 mg, 0.11 mmol) (WO2010132538) and (R)-5-((1H-1,2,3-triazol-1-yl)methyl)-3-(3-fluoro-4-(4,4,5,5-tetramethyl-1,3,2-dioxaborolan-2-yl)phenyl)oxazolidin-2-one) (T. Komine et al. *J. Med. Chem.,* 2008, 51, 6558) (43 mg, 0.11 mmol), according to the same method of Example 1.

$^1$H NMR (DMSO-d6, 400 MHz) δ11.93 (br s, 1H), 10.01 (s, 1H), 8.19 (d, J=1.0 Hz, 1H), 7.77 (d, J=1.0 Hz, 1H), 7.71 (d, J=8.7 Hz, 2H), 7.57-7.49 (m, 4H), 7.43-7.30 (m, 5H), 7.29-7.14 (m, 1H), 5.51 (d, J=7.9 Hz, 1H), 5.20-5.14 (m, 1H), 4.86 (d, J=5.1 Hz, 2H), 4.42 (dd, J=3.2, 8.1 Hz, 1H), 4.28 (t, J=9.2 Hz, 1H), 3.95 (dd, J=5.7, 9.5 Hz, 1H), 3.85-3.81 (m, 1H), 3.54 (s, 3H), 3.20 (q, J=8.1 Hz, 1H), 2.06-1.80 (m, 5H).

Example 5 methyl ((S)-1-((S)-2-(5-(2'-fluoro-4'-((R)-5-((4-(hydroxymethyl)-1H-1,2,3-triazole-1-yl)methyl)-2-oxoxazolidin-3-yl)-[1,1'-biphenyl]-4-yl)-1H-imidazole-2-yl)pyrrolidine-1-yl)-3-methyl-1-oxobutane-2-yl)carbamate[Methyl ((S)-1-((S)-2-(5-(2'-fluoro-4'-((R)-5-((4-(hydroxymethyl)-1H-1,2,3-triazol-1-yl)methyl)-2-oxooxazolidin-3-yl)-[1,1'-biphenyl]-4-yl)-1H-imidazol-2-yl)pyrrolidin-1-yl)-3-methyl-1-oxobutan-2-yl)carbamate]

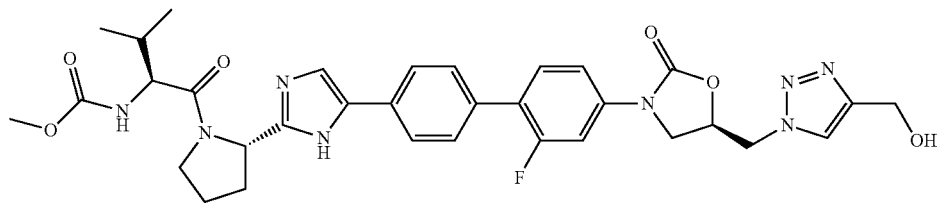

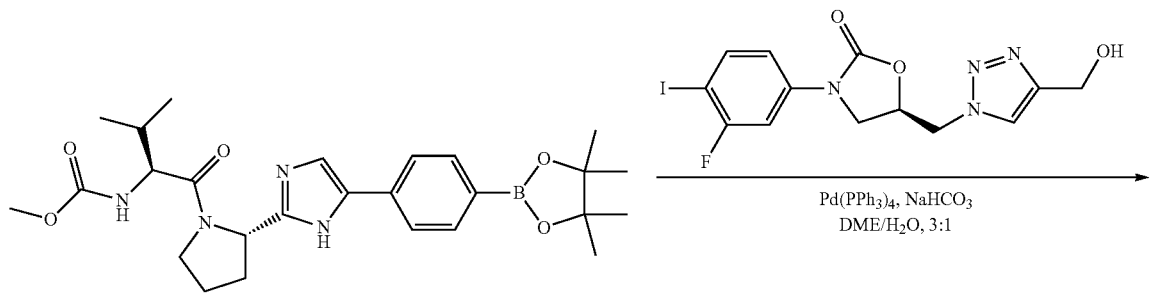

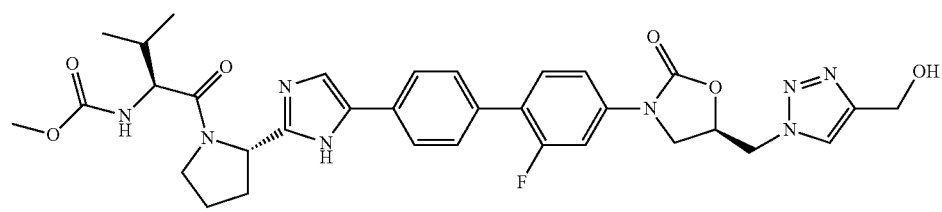

The subject compound (56 mg, 16%) was obtained from methyl ((S)-3-methyl-1-oxo-1-((S)-2-(5-(4-(4,4,5,5-tetramethyl-1,3,2-dioxaborolan-2-yl)phenyl)-1H-imidazol-2-yl)pyrrolidin-1-yl)butan-2-yl)carbamate (261 mg, 0.53 mmol) and (R)-3-(3-fluoro-4-iodophenyl)-5-((4-(hydroxymethyl)-1H-1,2,3-triazol-1-yl)methyl)oxazolidin-2-one (WO2004048350 (CuI/CH$_3$CN, 200 mg, 48 mmol), according to the same method of Example 1.

$^1$H NMR (300 MHz, DMSO): δ11.79 (s, 1H), 8.03 (s, 1H), 7.80 (d, J=8.2 Hz, 2H), 7.56 (m, 5H), 7.38 (m, 1H), 7.28 (d, J=8.4 Hz, 1H), 5.22 (t, J=5.7 Hz, 1H), 5.14 (m, 2H), 4.82 (d, J=5.3 Hz, 2H), 4.53 (d, J=5.6 Hz, 2H), 4.29 (t, J=9.1 Hz, 1H), 4.07 (t, J=8.3 Hz, 1H), 3.95 (dd, J=9.3, 6.0 Hz, 1H), 3.81 (s, 1H), 3.50 (s, 3H), 2.08 (m, 3H), 1.24 (s, 2H), 0.88 (m, 6H); $^{13}$C NMR (75 MHz, CDCl$_3$): δ172.32, 158.20, 157.51, 148.40, 137.74, 133.17, 130.06, 130.54, 130.29, 128.77, 124.47, 123.67, 113.35, 71.14, 57.86, 55.81, 54.75, 52.33, 47.92, 31.17, 29.69, 25.13, 19.26, 17.85.

Example 6 methyl ((S)-1-((S)-2-(5-(2'-fluoro-4'-((R)-5-((4-(2-hydroxyethyl)-1H-1,2,3-triazole-1-yl)methyl)-2-oxooxazolidin-3-yl)-[1,1'-biphenyl]-4-yl)-1H-imidazole-2-yl)pyrrolidine-1-yl)-3-methyl-1-oxobutane-2-yl)carbamate[Methyl ((S)-1-((S)-2-(5-(2'-fluoro-4'-((R)-5-((4-(2-hydroxyethyl)-1H-1,2,3-triazol-1-yl)methyl)-2-oxooxazolidin-3-yl)-[1,1'-biphenyl]-4-yl)-1H-imidazol-2-yl)pyrrolidin-1-yl)-3-methyl-1-oxobutan-2-yl)carbamate]

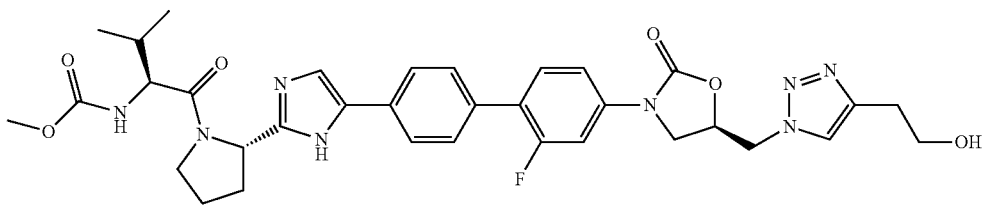 [SMILES: COC(=O)N[C@H](C(=O)N1CCC[C@H]1c1ncc(-c2ccc(-c3ccc(N4C[C@H](Cn5cc(CCO)nn5)OC4=O)cc3F)cc2)[nH]1)C(C)C]

Step (1). (R)-3-(3-fluoro-4-iodophenyl)-5-((4-(2-hydroxyethyl)-1H-1,2,3-triazol-1-yl)methyl)oxazolidin-2-one

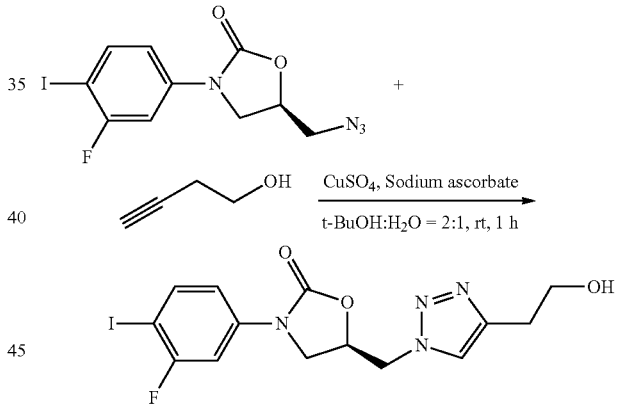

In Ar atmosphere, (R)-5-(azidomethyl)-3-(3-fluoro-4-iodophenyl)oxazolidin-2-one (WO 2003022824 or F. Reck, et al. J. Med. Chem. 2007, 50, 4868, 70 mg, 0.19 mmol) and but-3-yn-1-ol (27 mg, 0.38 mmol) were dissolved in t-BuOH/H$_2$O (1 mL: 0.5 mL), added with CuSO$_4$ (7 mg, 0.042 mmol) and Sodium ascorbate (8 mg, 0.042 mmol), and agitated at a room temperature for 1 hour. The reacting solution was concentrated under vacuum, added with H$_2$O (5 mL) and extracted with DCM (10 mL×2). Collected organic layer was washed with brine, dried with Na$_2$SO$_4$, filtrated and concentrated under vacuum. The concentrated product was purified with column chromatography ((MC: MeOH:H$_2$O:NH$_4$OH=280:20:1:1), to obtain the subject compound (86 mg).

$^1$H NMR (DMSO, 300 MHz): δ 8.62 (s, 1H), 7.82 (m, 2H), 7.47 (m, 3H), 7.35 (m, 1H), 7.16 (dd, J=8.7, 2.4 Hz, 1H), 5.21 (m, 1H), 4.87 (d, J=5.3 Hz, 1H), 4.27 (t, 1H), 3.95 (dd, J=9.4, 5.9 Hz, 1H); $^{13}$C NMR (100 MHz, DMSO): δ169.75, 162.80, 160.41, 153.83, 145.58, 140.56, 140.45, 139.57, 139.57, 124.22, 124.22, 116.25, 116.23, 106.11, 105.81, 75.00, 74.75, 71.57, 52.27, 47.42, 34.50, 22.87.

Step (2)

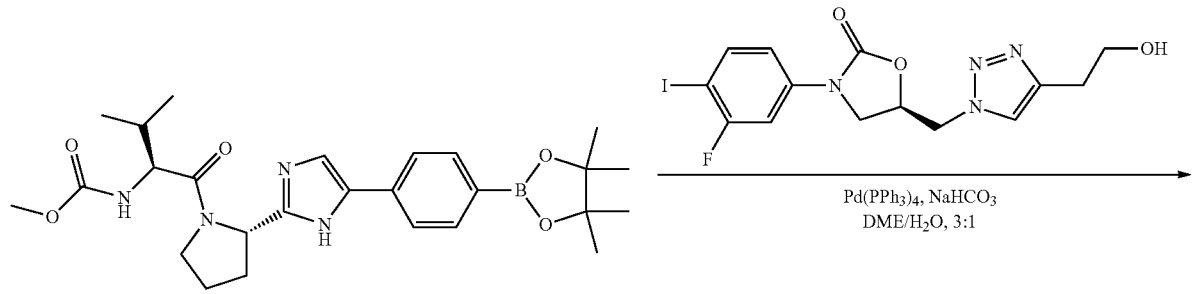

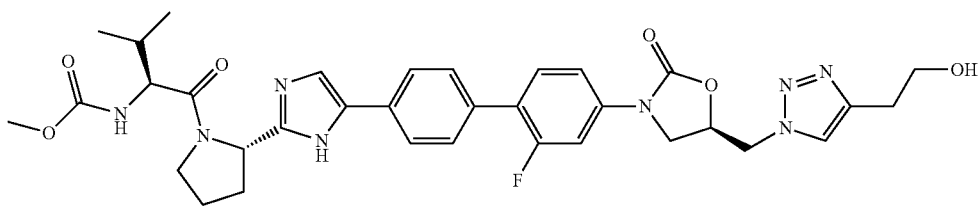

The subject compound (30 mg, 15%) was obtained from Methyl ((S)-3-methyl-1-oxo-1-((S)-2-(5-(4-(4,4,5,5-tetramethyl-1,3,2-dioxaborolan-2-yl)phenyl)-1H-imidazol-2-yl)pyrrolidin-1-yl)butan-2-yl)carbamate (110 mg, 0.22 mmol) and (R)-3-(3-fluoro-4-iodophenyl)-5-((4-(2-hydroxyethyl)-1H-1,2,3-triazol-1-yl)methyl)oxazolidin-2-one (86 mg, 0.20 mmol) produced in Step (1), according to the same method of Example 1

$^1$H NMR (400 MHz, DMSO): δ11.59 (s, 1H), 7.94 (s, 1H), 7.81 (d, J=8.0 Hz, 2H), 7.56 (m, 5H), 7.37 (m, 1H), 7.30 (d, J=8.4 Hz, 1H), 5.16 (m, 1H), 5.09 (m, 1H), 4.80 (d, J=5.2 Hz, 2H), 4.72 (d, J=5.2 Hz, 1H), 4.30 (t, J=9.2 Hz, 1H), 4.08 (t, J=9.4 Hz, 1H), 3.94 (dd, J=9.4, 5.8 Hz, 1H), 3.82 (m, 2H), 3.54 (m, 2H), 3.61 (m, 2H), 3.54 (s, 3H), 2.77 (m, 2H), 2.16 (m, 2H), 1.98 (m, 2H), 0.89 (m, 6H); $^{13}$C NMR (75 MHz, DMSO): δ 172.58, 157.18, 153.42, 146.27, 130.63, 128.99, 123.40, 113.70, 106.64, 106.26, 70.69 (m), 61.40, 57.74, 54.57, 52.39, 52.19, 47.94, 47.30, 33.95, 31.60, 31.25, 30.95, 29.72, 28.78, 27.96, 25.32, 24.96, 22.67, 19.26, 17.68, 14.14.

Example 7 methyl ((S)-1-((S)-2-(5-(2'-fluoro-4'-((R)-5-((4-(methoxymethyl)-1H-1,2,3-triazole-1-yl)methyl)-2-oxoxazolidin-3-yl)-[1,1'-biphenyl]-4-yl)-1H-imidazole-2-yl)pyrrolidine-1-yl)-3-methyl-1-oxobutane-2-yl)carbamate[Methyl ((S)-1-((S)-2-(5-(2'-fluoro-4'-((R)-5-((4-(methoxymethyl)-1H-1,2,3-triazol-1-yl)methyl)-2-oxooxazolidin-3-yl)-[1,1'-biphenyl]-4-yl)-1H-imidazol-2-yl)pyrrolidin-1-yl)-3-methyl-1-oxobutan-2-yl)carbamate]

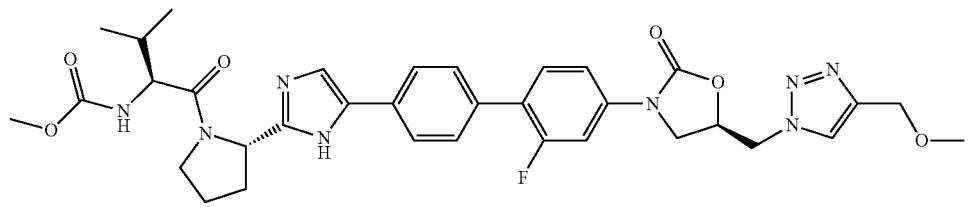

Step (1): (R)-3-(3-fluoro-4-iodophenyl)-5-((4-(methoxymethyl)-1H-1,2,3-triazol-1-yl)methyl)oxazolidin-2-one

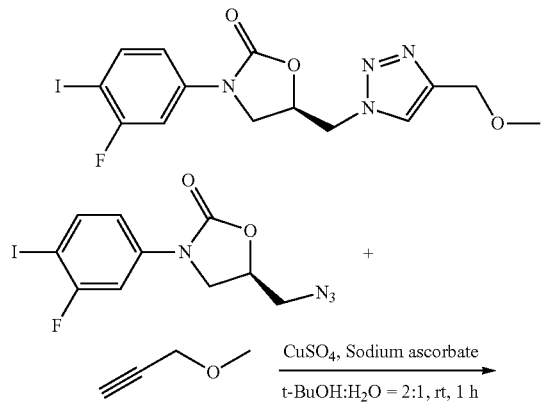

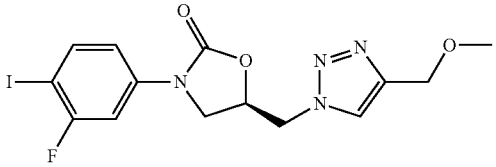

The subject compound (64 mg, 79%) was obtained from (R)-5-(Azidomethyl)-3-(3-fluoro-4-iodophenyl)oxazolidin-2-one (70 mg, 0.19 mmol) and 3-methoxyprop-1-yne (27 mg, 0.38 mmol), according to the same method of Step (1) in Example 6.

$^1$H NMR (DMSO, 300 MHz): δ8.13 (s, 1H), 7.82 (t, J=7.8 Hz, 1H), 7.49 (d, J=10.8 Hz, 1H), 7.15 (d, J=8.9 Hz, 1H), 5.14 (m, 1H), 4.80 (d, J=4.9 Hz, 1H), 4.23 (t, J=9.3 Hz, 1H), 3.89 (dd, J=8.6 Hz, 6.0 Hz, 1H), 3.22 (s, 3H); $^{13}$C-NMR (75 MHz, DMSO): δ198.10, 181.90, 153.79, 144.38, 140.55, 140.41, 139.57, 125.35, 116.24, 116.19, 106.15, 106.76, 75.05, 74.71, 71.45, 65.21, 57.65, 52.29, 47.41.

Step (2)

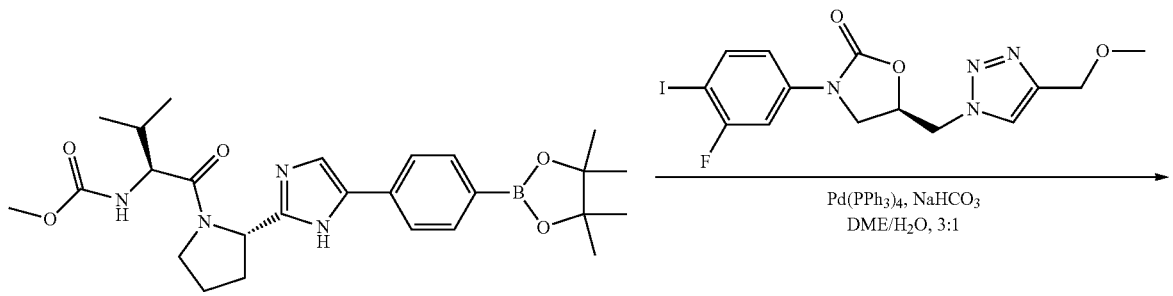

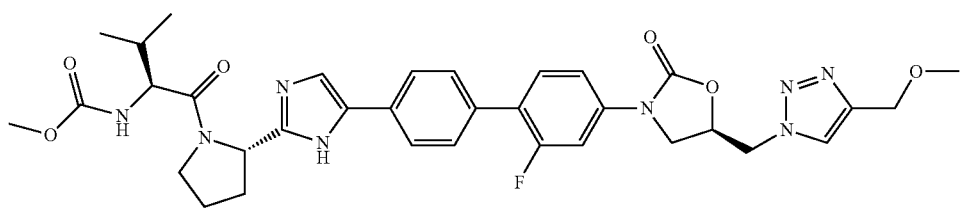

The subject compound (25 mg, 25%) was obtained from methyl ((S)-3-methyl-1-oxo-1-((S)-2-(5-(4-(4,4,5,5-tetramethyl-1,3,2-dioxaborolan-2-yl)phenyl)-1H-imidazol-2-yl)pyrrolidin-1-yl)butan-2-yl)carbamate (81 mg, 0.10 mmol) and (R)-3-(3-fluoro-4-iodophenyl)-5-((4-(methoxymethyl)-1H-1,2,3-triazol-1-yl)methyl)oxazolidin-2-one (64 mg, 0.15 mmol) prepared in Step (1), according to the same method of Example 1.

$^1$H NMR (300 MHz, DMSO): δ 11.56 (br s, 1H), 8.05 (s, 1H), 7.72 (d, J=8.0 Hz, 1H), 7.34 (m, 5H), 5.44 (m, 1H), 5.07 (m, 1H), 4.82 (d, J=4.3 Hz, 1H), 4.50 (m, 4H), 4.30 (m, 1H), 4.04 (d, J=6.9 Hz, 2H), 3.80 (m, 1H), 3.53 (s, 3H), 3.05 (m, 2H), 2.12 (m, 3H), 2.08 (m, 2H), 0.86 (m, 6H); $^{13}$C NMR (75 MHz, CDCl$_3$): δ 172.72, 157.17, 153.25, 148.23, 145.83, 144.99, 131.80, 128.80, 124.17, 124.07, 113.41, 109.53, 109.20, 100.54, 100.18, 53.81, 52.42, 52.18, 47.93, 47.24, 46.87, 46.77, 31.20, 29.72, 27.41, 25.39, 19.26, 18.46, 17.59.

Example 8

1-(((R)-3-(2-fluoro-4'-(2-((S)-1-((methoxycarbonyl)-L-valyl)pyrrolidine-2-yl)-1H-imidazole-5-yl)-[1,1'-biphenyl]-4-yl)-2-oxooxazolidine-5-yl)methyl)-1H-1,2,3-triazole-4-yl)methyl acetate[1-(((R)-3-(2-Fluoro-4'-(2-((S)-1-((methoxycarbonyl)-L-valyl)pyrrolidin-2-yl)-1H-imidazol-5-yl)-[1,1'-biphenyl]-4-yl)-2-oxooxazolidin-5-yl)methyl)-1H-1,2,3-triazol-4-yl)methyl acetate]

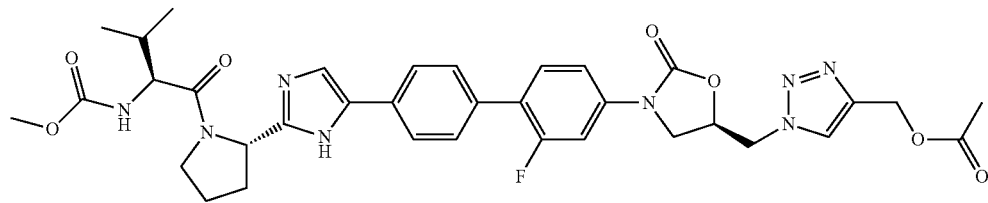 [SMILES: COC(=O)N[C@H](C(=O)N1CCC[C@H]1c1ncc(-c2ccc(-c3ccc(N4C[C@H](Cn5cc(COC(C)=O)nn5)OC4=O)cc3F)cc2)[nH]1)C(C)C]

Step (1). (R)-(1-((3-(3-fluoro-4-iodophenyl)-2-oxooxazolidin-5-yl)methyl)-1H-1,2,3-triazol-4-yl) methyl acetate

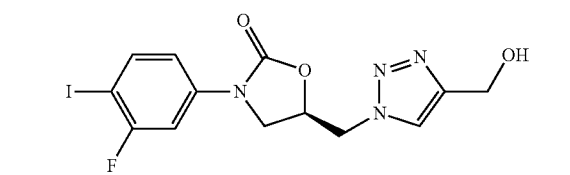

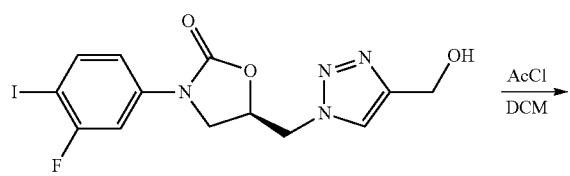

In Ar atmosphere, (R)-3-(3-fluoro-4-iodophenyl)-5-((4-(hydroxymethyl)-H-1,2,3-triazol-1-yl)methyl)oxazolidin-2-one (50 mg, 0.12 mmol) was dissolved in DCM (1.2 ml) and added in a dropwise manner at 0° C. with acetyl chloride (10 mg, 0.13 mmol) and triethylamine (18 mg, 0.18 mmol). The mixture was agitated at a room temperature for 2 hours and the reaction termination was confirmed by TLC(DCM:MeOH=30:1). The reaction solution was added with H₂O (5 mL) and extracted with DCM (10 mL×2). The collected organic layer was washed with brine, dried with Na₂SO₄, filtered and concentrated under vacuum. The concentrated product was purified with column chromatography ((MC:MeOH:H₂O:NH₄OH=280:20:1:1), to obtain the subject compound (25 mg, 45%).

$^1$H NMR (CDCl$_3$, 300 MHz): δ7.90 (s, 1H), 7.70 (dd, J=8.7, 2.4 Hz, 1H), 7.38 (dd, J=10.1, 2.5 Hz, 1H), 6.94 (dd, J=8.7, 2.4 Hz, 1H), 5.21 (s, 2H), 5.11 (m, 1H), 4.79 (t, J=4.3 Hz, 1H), 4.21 (t, J=9.1 Hz, 1H), 3.96 (dd, J=9.4, 6.2 Hz, 1H), 2.09 (s, 3H); $^{13}$C-NMR (75 MHz, DMSO): δ 170.78, 6163.49, 162.33, 160.24, 152.97, 143.71, 139.39, 139.35, 139.28, 139.15, 125.26, 115.16, 115.11, 106.37, 105.98, 70.43, 57.34, 52.16, 47.17, 20.83.

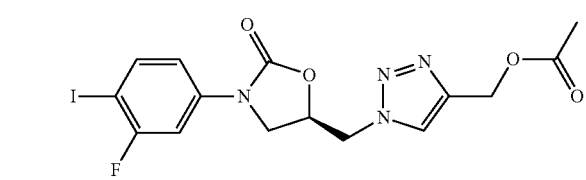

Step (2)

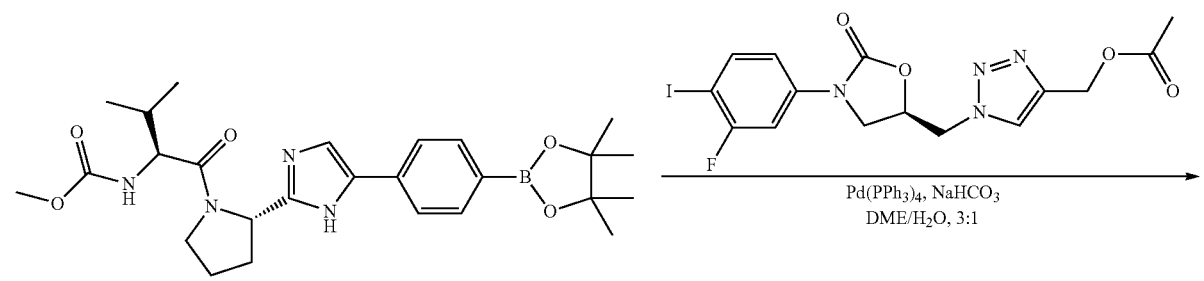

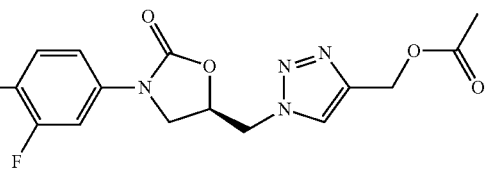

The subject compound (38 mg, 17%) was obtained from methyl ((S)-3-methyl-1-oxo-1-((S)-2-(5-(4-(4,4,5,5-tetramethyl-1,3,2-dioxaborolan-2-yl)phenyl)-1H-imidazol-2-yl)pyrrolidin-1-yl)butan-2-yl)carbamate (150 mg, 0.31 mmol) and (R)-(1-((3-(3-fluoro-4-iodophenyl)-2-oxooxazolidin-5-yl)methyl)-1H-1,2,3-triazol-4-yl)methyl acetate (130 mg, 0.28 mmol) prepared in Step (1), according to the same method of Example 1.

$^1$H NMR (300 MHz, DMSO): δ 11.82 (s, 1H), 8.03 (s, 1H), 7.80 (d, J=8.2 Hz, 2H), 7.55 (m, 5H), 7.34 (m, 2H), 5.24 (t, J=5.6 Hz, 1H), 5.16 (m, 1H), 5.11 (m, 1H), 4.82 (d, J=5.3 Hz, 2H), 4.52 (d, J=5.5 Hz, 2H), 4.28 (m, 1H), 4.06 (m, 1H), 3.94 (m, 1H), 3.81 (m, 1H), 3.53 (s, 3H), 2.15 (m, 2H), 1.96 (m, 4H), 1.05 (t, J=7.0 Hz, 1H), 0.87 (m, 7H); $^{13}$C NMR (75 MHz, CDCl$_3$): δ172.43, 157.21, 153.50, 148.33, 137.78, 137.64, 130.32, 128.87, 124.75, 123.62, 113.41, 57.91, 55.80, 54.80, 52.37, 47.92, 47.25, 31.95, 31.61, 31.21, 29.72, 29.09, 25.15, 22.68, 19.26, 17.86, 14.15.

Example 9 methyl ((S)-1-((S)-2-(5-(4'-((R)-5-((4-((benzyloxy)methyl)-1H-1,2,3-triazole-1-yl)methyl)-2-oxoxazolidin-3-yl)-2'-fluoro-[1,1'-biphenyl]-4-yl)-1H-imidazole-2-yl)pyrrolidine-1-yl)-3-methyl-1-oxobutane-2-yl)carbamate[Methyl ((S)-1-((S)-2-(5-(4'-((R)-5-((4-((benzyloxy)methyl)-1H-1,2,3-triazol-1-yl)methyl)-2-oxooxazolidin-3-yl)-2'-fluoro-[1,1'-biphenyl]-4-yl)-1H-imidazol-2-yl)pyrrolidin-1-yl)-3-methyl-1-oxobutan-2-yl)carbamate]

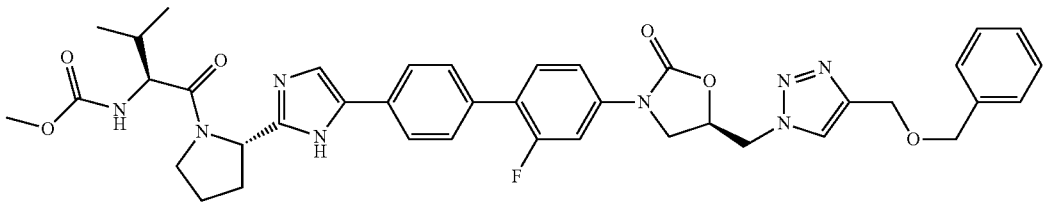 [SMILES: COC(=O)N[C@H](C(=O)N1CCC[C@H]1c1ncc(-c2ccc(-c3ccc(N4C[C@H](Cn5cc(COCc6ccccc6)nn5)OC4=O)cc3F)cc2)[nH]1)C(C)C]

Step (1). (R)-5-((4-((benzyloxy)methyl)-1H-1,2,3-triazol-1-yl)methyl)-3-(3-fluoro-4-iodophenyl)oxazolidin-2-one

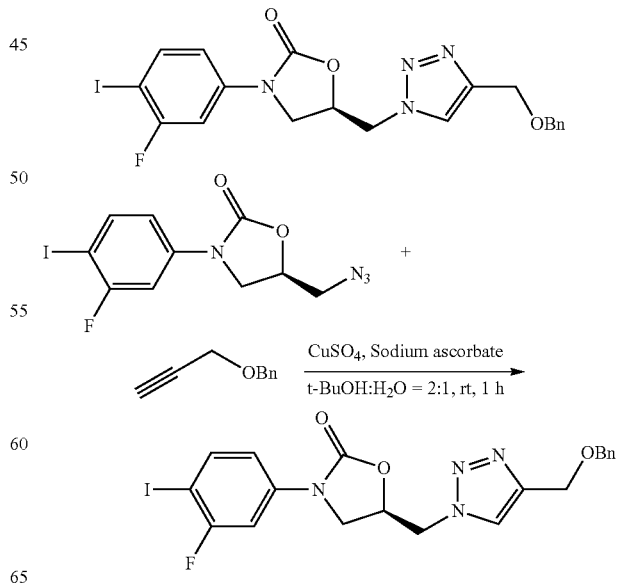

The subject compound (66 mg, 93%) was obtained from (R)-5-(Azidomethyl)-3-(3-fluoro-4-iodophenyl)oxazolidin-2-one (50 mg, 0.14 mmol) and ((prop-2-yn-1-yloxy)methyl)benzene (41 mg, 0.28 mmol).

$^1$H NMR (DMSO, 400 MHz): δ 8.20 (s, 1H), δ7.80 (t, J=8.0 Hz, 1H), 7.51 (dd, 1H), 7.35 (m, 5H), 7.15 (dd, 1H), 5.17 (m, 1H), 4.84 (d, 1H), 4.58 (s, 1H), 4.49 (s, 1H), 4.25 (t, 1H), 3.92 (dd, 1H).

Step (2)

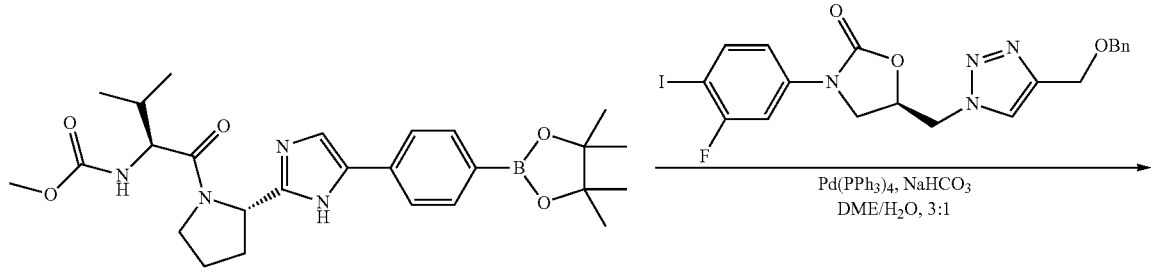

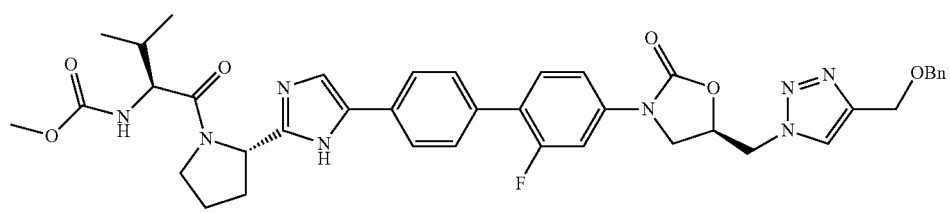

The subject compound (20 mg, 20%) was obtained from methyl ((S)-3-methyl-1-oxo-1-((S)-2-(5-(4-(4,4,5,5-tetramethyl-1,3,2-dioxaborolan-2-yl)phenyl)-1H-imidazol-2-yl)pyrrolidin-1-yl)butan-2-yl)carbamate (64 mg, 0.13 mmol) and (R)-5-((4-((benzyloxy)methyl)-1H-1,2,3-triazol-1-yl)methyl)-3-(3-fluoro-4-iodophenyl) oxazolidin-2-one (60 mg, 0.12 mmol) prepared in Step (1), according to the same method of Example 1.

$^1$H NMR (300 MHz, DMSO): δ 11.83 (br s, 1H), 8.22 (s, 1H), 7.50 (m, 4H), 7.34 (m, 10H), 5.31 (m, 1H), 4.84 (d, J=4.4 Hz, 1H), 4.01 (m, J=4.4 Hz, 2H), 4.53 (m, 6H), 4.20 (m, 1H), 3.80 (m, 1H), 3.53 (m, 3H), 2.27 (m, 2H), 1.98 (m, 3H), 0.87 (m, 6H); $^{13}$C NMR (75 MHz, CDCl$_3$): δ161.81, 160.98, 158.50, 157.14, 156.98, 153.22, 149.67, 145.92, 145.04, 139.59, 138.65, 137.76, 134.86, 133.99, 132.84, 132.02, 131.79, 130.70, 128.93, 124.91, 124.31, 120.5, 113.78, 123.46, 112.37, 109.18, 106.66, 75.61, 72.66, 70.54, 68.44, 63.61, 57.67, 54.48, 53.73, 52.38, 52.10, 47.90, 47.22, 46.75, 31.22, 29.70, 27.40, 25.36, 19.24, 17.60.

Example 10 methyl ((S)-1-((S)-2-(5-(4'-((R)-5-((4-(acetamidomethyl)-1H-1,2,3-triazole-1-yl)methyl)-2-oxoxazolidin-3-yl)-2'-fluoro-[1,1'-biphenyl]-4-yl)-1H-imidazole-2-yl)pyrrolidine-1-yl)-3-methyl-1-oxobutane-2-yl)carbamate[Methyl ((S)-1-((S)-2-(5-(4'-((R)-5-((4-(acetamidomethyl)-1H-1,2,3-triazol-1-yl)methyl)-2-oxooxazolidin-3-yl)-2'-fluoro-[1,1'-biphenyl]-4-yl)-1H-imidazol-2-yl)pyrrolidin-1-yl)-3-methyl-1-oxobutan-2-yl)carbamate]

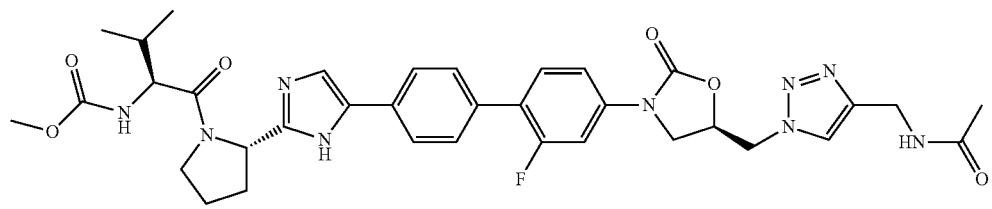 [SMILES: COC(=O)N[C@H](C(=O)N1CCC[C@H]1c1ncc(-c2ccc(-c3ccc(N4C[C@H](Cn5cc(CNC(C)=O)nn5)OC4=O)cc3F)cc2)[nH]1)C(C)C]

Step (1). (R)—N-((1-((3-(3-fluoro-4-iodophenyl)-2-oxooxazolidin-5-yl)methyl)-1H-1,2,3-triazol-4-yl)methyl)acetamide

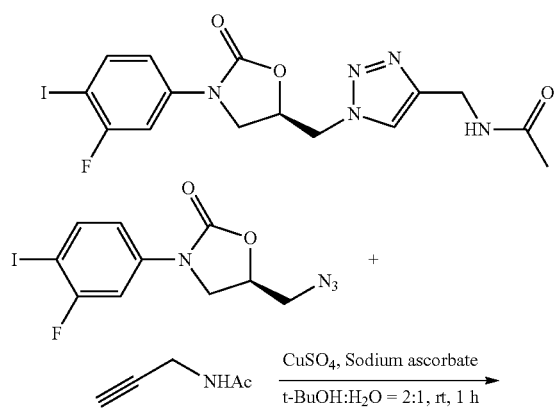

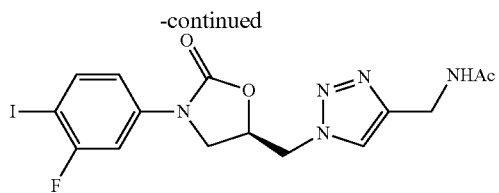

The subject compound (92 mg, 72%) was obtained from (R)-5-(azidomethyl)-3-(3-fluoro-4-iodophenyl)oxazolidin-2-one (100 mg, 0.28 mmol) and N-(prop-2-yn-1-yl)acetamide (53 mg, 0.56 mmol).

$^1$H NMR (DMSO, 300 MHz): δ8.35 (m, 1H), 7.96 (s, 1H), 7.82 (t, J=8.0 Hz, 1H), 7.51 (dd, J=10.9, 2.3 Hz, 5H), 7.16 (dd, J=8.7, 2.4 Hz, 1H), 5.16-5.08 (m, 1H), 4.78 (d, J=5.5 Hz, 1H), 4.27-4.19 (m, 3H), 3.87 (dd, J=9.3, 6.0 Hz, 1H), 1.82 (s, 3H); $^{13}$C-NMR (100 MHz, DMSO): δ169.75, 162.80, 160.41, 153.83, 145.58, 140.56, 140.45, 139.57, 139.54, 124.22, 116.25, 116.23, 106.81, 75.00, 74.75, 71.57, 52.27, 47.42, 22.87.

Step (2)

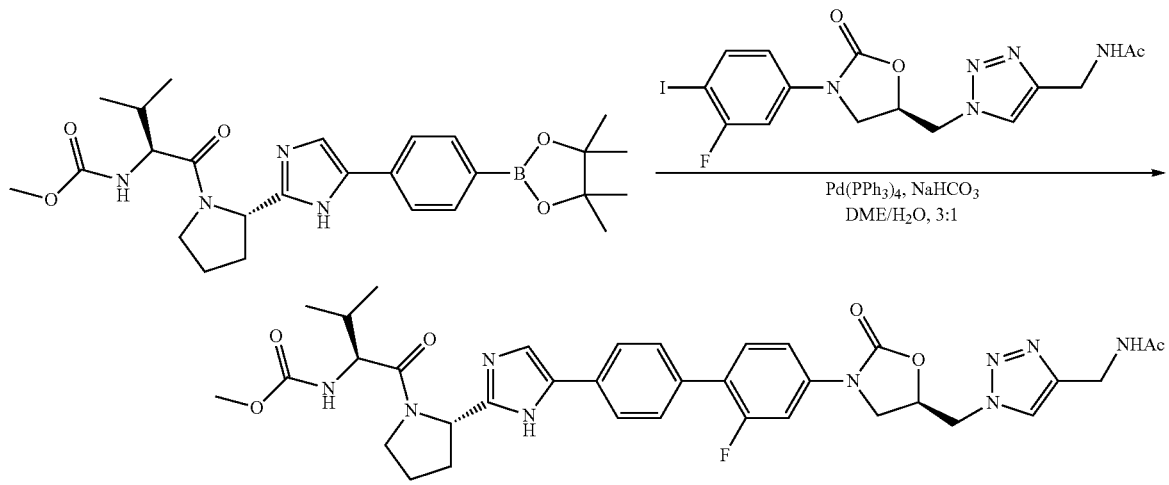

The subject compound (26 mg, 19%) was obtained from methyl ((S)-3-methyl-1-oxo-1-((S)-2-(5-(4-(4,4,5,5-tetramethyl-1,3,2-dioxaborolan-2-yl)phenyl)-1H-imidazol-2-yl)pyrrolidin-1-yl)butan-2-yl) carbamate (110 mg, 0.022 mmol) and (R)—N-((1-((3-(3-fluoro-4-iodophenyl)-2-oxooxazolidin-5-yl)methyl)-1H-1,2,3-triazol-4-yl)methyl) acetamide (92 mg, 0.20 mmol) prepared in Step (1).

$^1$H NMR (300 MHz, DMSO): δ11.79 (s, 1H), 8.36 (m, 1H), 7.99 (s, 1H), 7.80 (d, J=8.2 Hz, 2H), 7.58 (m, 5H), 7.38 (d, J=8.6 Hz, 1H), 7.27 (d, J=8.6 Hz, 1H), 5.17 (m, 1H), 5.11 (m, 1H), 4.81 (d, J=5.2 Hz, 2H), 4.29 (m, 3H), 4.07 (t, J=8.0 Hz, 1H), 3.94 (dd, J=9.2, 6.1 Hz, 1H), 3.81 (s, 2H), 3.5s (s, 3H), 2.16 (m, 2H), 1.94 (m, 6H), 0.87 (m, 6H); $^{13}$C NMR (75 MHz, CDCl$_3$): δ172.49, 170.42, 158.01, 157.16, 153.34, 145.46, 130.61, 128.93, 124.70, 123.88, 113.52, 106.50, 106.11, 70.66, 57.77, 54.66, 52.38, 47.93, 47.34, 34.95, 31.26, 29.71, 28.30, 25.27, 23.07, 19.27, 17.73.

Example 11 methyl ((S)-1-((S)-2-(5-(2'-fluoro-4'-((R)-2-oxo-5-((4-phenyl-H-1,2,3-triazole-1-yl)methyl)oxazolidine-3-yl)-[1,1'-biphenyl]-4-yl)-1H-imidazole-2-yl)pyrrolidine-1-yl)-3-methyl-1-oxobutane-2-yl)carbamate
[Methyl ((S)-1-((S)-2-(5-(2'-fluoro-4'-((R)-2-oxo-5-((4-phenyl-1H-1,2,3-triazole-1-yl)methyl)oxazolidin-3-yl)-[1,1'-biphenyl]-4-yl)-1H-imidazol-2-yl)pyrrolidin-1-yl)-3-methyl-1-oxobutan-2-yl) carbamate]

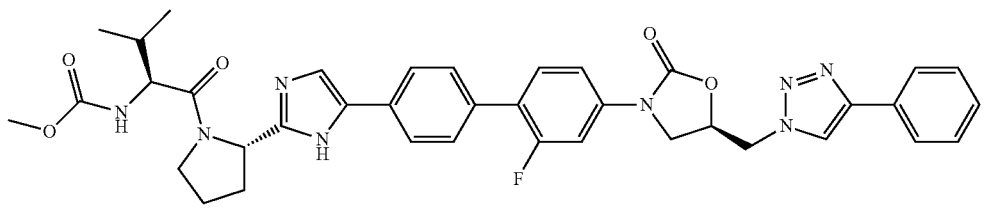 [SMILES: COC(=O)N[C@H](C(=O)N1CCC[C@H]1c1ncc(-c2ccc(-c3ccc(N4C[C@H](Cn5cc(-c6ccccc6)nn5)OC4=O)cc3F)cc2)[nH]1)C(C)C]

Step (1). (R)-3-(3-fluoro-4-iodophenyl)-5-((4-phenyl-H-1,2,3-triazol-1-yl)methyl)oxazolidin-2-one

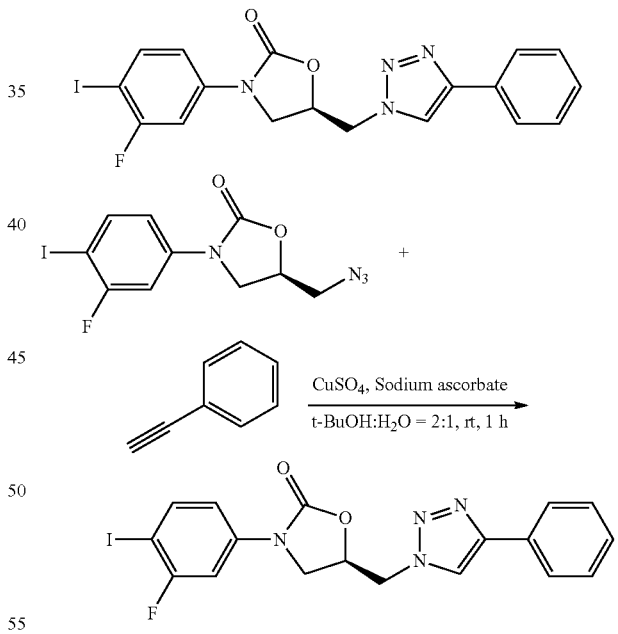

The subject compound (81 mg, 92%) was obtained from (R)-5-(azidomethyl)-3-(3-fluoro-4-iodophenyl)oxazolidin-2-one (70 mg, 0.19 mmol) and ethynylbenzene (39 mg, 0.38 mmol).

$^1$H NMR (CDCl$_3$, 300 MHz): δ 8.62 (s, 1H), δ7.76 (m, 2H), 7.47 (m, 3H), 7.36 (m, 1H), 7.16 (dd, J=8.7, 2.4 Hz, 1H), 5.21 (m, 1H), 4.87 (d, J=5.3 Hz, 1H), 4.27 (t, 1H), 3.95 (dd, J=9.4, 5.9 Hz, 1H); $^{13}$C-NMR (100 MHz, CDCl$_3$): δ162.80, 160.41, 153.83, 146.90, 140.55, 139.53, 130.94, 129.39, 128.46, 125.69, 122.82, 116.24, 116.21, 106.11, 105.81, 75.06, 74.80, 71.47, 52.53, 47.51.

Step (2)

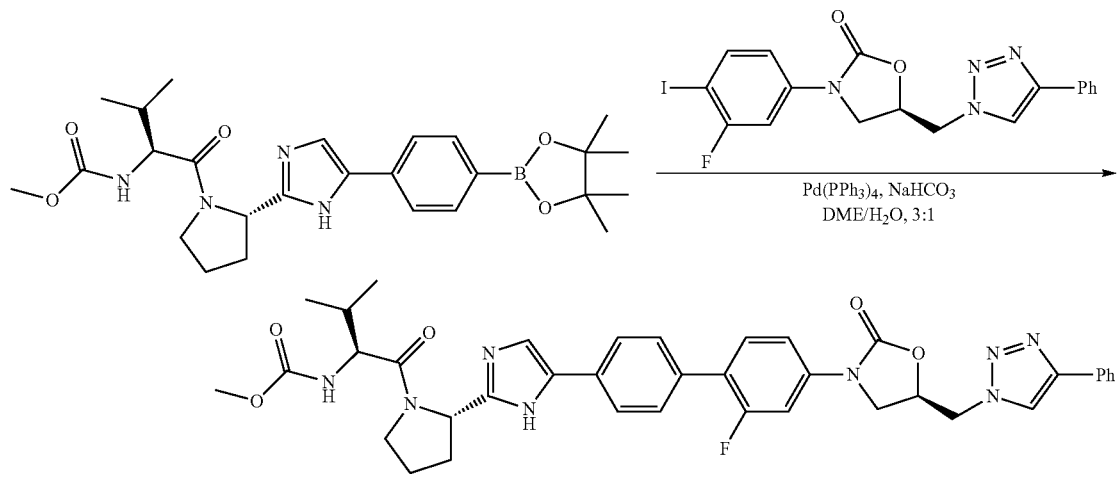

The subject compound (21.5 mg, 16%) was obtained from Methyl ((S)-3-methyl-1-oxo-1-((S)-2-(5-(4-(4,4,5,5-tetramethyl-1,3,2-dioxaborolan-2-yl)phenyl)-1H-imidazol-2-yl)pyrrolidin-1-yl)butan-2-yl) carbamate (93 mg, 0.19 mmol) and (R)-3-(3-fluoro-4-iodophenyl)-5-((4-phenyl-1H-1,2,3-triazol-1-yl)methyl)oxazolidin-2-one (81 mg, 0.17) prepared in Step (1), according to the same method of Example 1.

$^1$H NMR (300 MHz, DMSO): δ11.82 (s, 1H), 8.65 (s, 1H), 7.82 (m, 4H), 7.45 (m, 10H), 5.23 (m, 1H), 4.89 (d, J=5.0 Hz, 2H), 4.34 (t, J=9.2 Hz, 1H), 4.03 (m, 2H), 3.80 (m, 2H), 3.53 (s, 3H), 2.14 (m, 2H), 1.95 (m, 3H), 0.87 (m, 6H); $^{13}$C NMR (75 MHz, CDCl$_3$): δ170.86, 153.93, 149.80, 146.90, 139.15, 134.95, 130.97, 129.39, 128.98, 128.45, 125.69, 124.73, 122.86, 114.56, 113.14, 106.40, 106.02, 73.97, 71.45, 58.45, 54.69, 52.60, 51.89, 47.58, 47.28, 31.34, 30.31, 25.42, 24.70, 19.41, 18.98.

Example 12 methyl ((S)-1-((S)-2-(5-(4'-((S)-5-(acetamidomethyl)-2-oxazolidine-3-yl)-2'-fluoro-[1,1'-biphenyl]-4-yl)-1H-imidazole-2-yl)pyrrolidine-1-yl)-3-methyl-1-oxobutane-2-yl)carbamate[Methyl ((S)-1-((S)-2-(5-(4'-((S)-5-(acetamidomethyl)-2-oxooxazolidin-3-yl)-2'-fluoro-[1,1'-biphenyl]-4-yl)-1H-imidazol-2-yl)pyrrolidin-1-yl)-3-methyl-1-oxobutan-2-yl) carbamate]

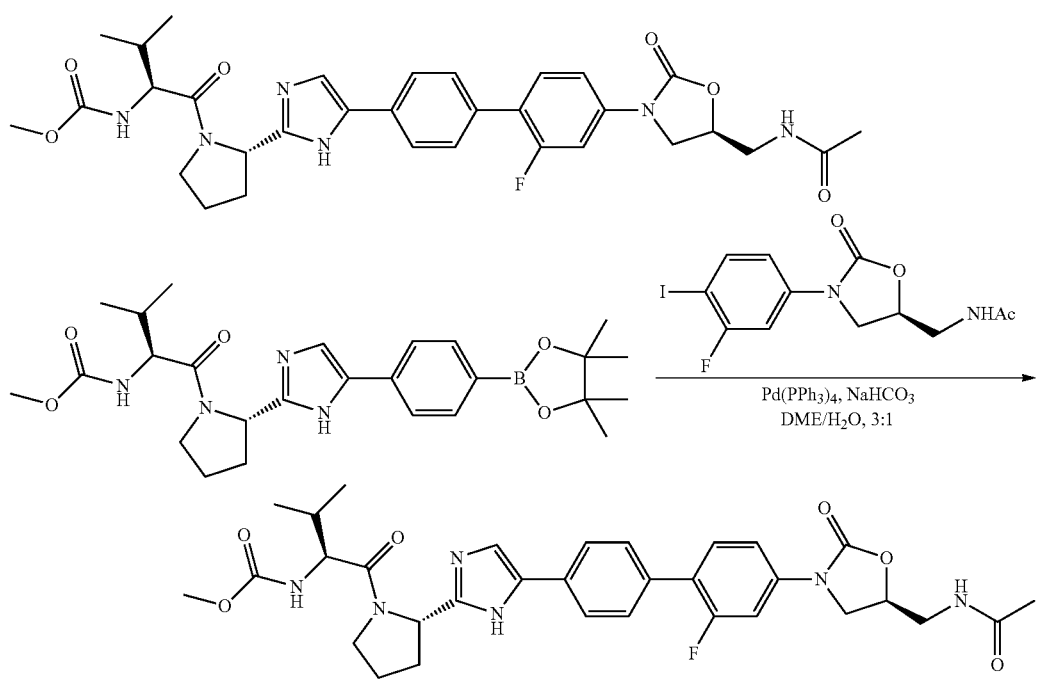

The subject compound (14 mg, 23%) was obtained from methyl ((S)-3-methyl-1-oxo-1-((S)-2-(5-(4-(4,4,5,5-tetramethyl-1,3,2-dioxaborolan-2-yl)phenyl)-1H-imidazol-2-yl)pyrrolidin-1-yl)butan-2-yl) carbamate (50 mg, 0.1 mmol) and (S)—N-((3-(3-fluoro-4-iodophenyl)-2-oxooxazolidin-5-yl)methyl)acetamide (WO 2001094342 34 mg, 0.1 mmol), according to the same method of Example 1.

¹H NMR (400 MHz, DMSO): δ11.81 (br s, 1H), 8.27 (t, J=5.8 Hz, 1H), 7.81 (d, J=6.8 Hz, 1H), 7.58 (m, 5H), 7.42 (d, J=8.4, 4.2 Hz, 1H), 7.29 (d, J=8.4 Hz, 1H), 5.09 (m, 1H), 4.78 (m, 1H), 4.19 (t, J=9.0 Hz, 1H), 4.08 (t, J=8.2 Hz, 1H), 3.81 (m, 2H), 3.56 (s, 3H), 3.46 (t, J=5.4 Hz, 2H), 2.09 (m, 2H), 1.98 (m, 3H), 1.86 (s, 3H), 0.92 (m, 6H); ¹³C NMR (75 MHz, DMSO): δ170.84, 170.49, 161.09, 157.85, 157.26, 154.47, 149.79, 139.53, 139.35, 139.18, 134.93, 131.08, 131.01, 129.00, 125.57, 124.72, 123.20, 114.44, 113.10, 106.24, 105.86, 72.22, 52.45, 55.37, 54.68, 51.86, 47.66, 47.28, 41.87, 31.36, 30.30, 24.71, 22.91, 19.42, 22.91, 19.42, 18.96.

Example 13 tert-butyl (S)-2-(5-(4'-((S)-5-(acetamidomethyl)-2-oxooxazolidin-3-yl)-2'-fluoro-[1,1'-biphenyl]-4-yl)-1H-imidazole-2-yl)pyrrolidine-1-carboxylate[tert-Butyl (S)-2-(5-(4'-((S)-5-(acetamidomethyl)-2-oxooxazolidin-3-yl)-2'-fluoro-[1,1'-biphenyl]-4-yl)-1H-imidazol-2-yl)pyrrolidine-1-carboxylate]

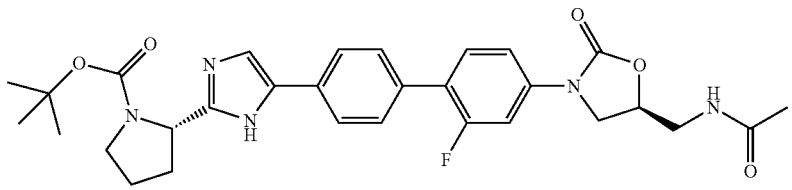

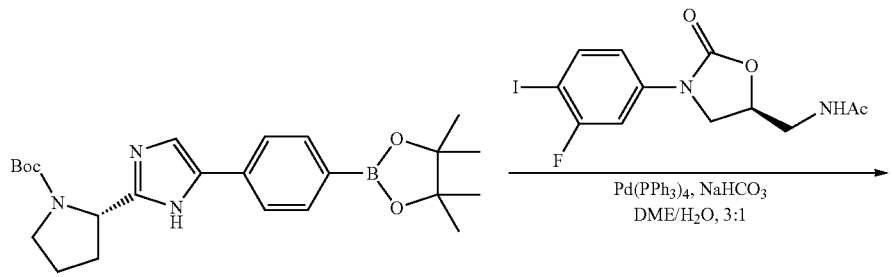

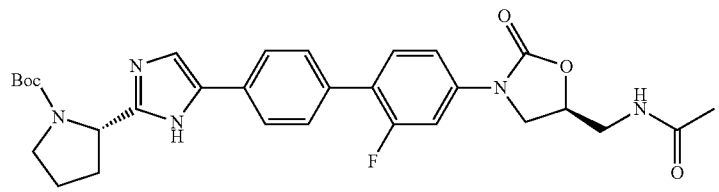

The subject compound (37 mg, 60%) was obtained from (S)-tert-Butyl 2-(5-(4-(4,4,5,5-tetramethyl-1,3,2-dioxaborolan-2-yl)phenyl)-1H-imidazol-2-yl)pyrrolidine-1-carboxylate (WO 2010096462, 60 mg, 0.1 mmol) and (S)—N-((3-(3-fluoro-4-iodophenyl)-2-oxooxazolidin-5-yl)methyl)acetamide (WO 2001094342, 37 mg, 0.1 mmol), according to the same method of Example 1.

¹H-NMR (400 MHz, DMSO): δ11.91 (br s, 1H), 8.27 (t, J=5.8 Hz, 1H), 7.85 (d, J=8.4 Hz, 1H), 7.58 (m, 5H), 7.42 (dd, J=8.4, 2.0 Hz, 1H), 4.77 (m, 1H), 4.20 (m, 3H), 3.80 (dd, J=9.0, 6.6 Hz, 1H), 3.45 (m, 1H), 1.86 (s, 3H), 1.42 (s, 9H); ¹³C NMR (100 MHz, DMSO): δ 172.58, 171.02, 170.49, 168.69, 163.05, 160.70, 158.27, 156.14, 154.47, 146.62, 139.53, 139.39, 134.80, 132.37, 131.07, 131.02, 129.47, 129.07, 124.78, 124.44, 123.35, 123.22, 114.45, 113.61, 106.20, 105.91, 78.53, 72.22, 47.66, 41.87, 38.46, 28.71, 28.71, 22.91.

Example 14

N—(((S)-3-(4'-(2-((S)-1-acetylpyrrolidine-2-yl)-1H-imidazole-5-yl)-2-fluoro-[1,1'-biphenyl]-4-yl)-2-oxooxazolidine-5-yl)methyl)acetamide[N—(((S)-3-(4'-(2-((S)-1-acetylpyrrolidin-2-yl)-H-imidazol-5-yl)-2-fluoro-[1,1'-biphenyl]-4-yl)-2-oxooxazolidin-5-yl)methyl)acetamide]

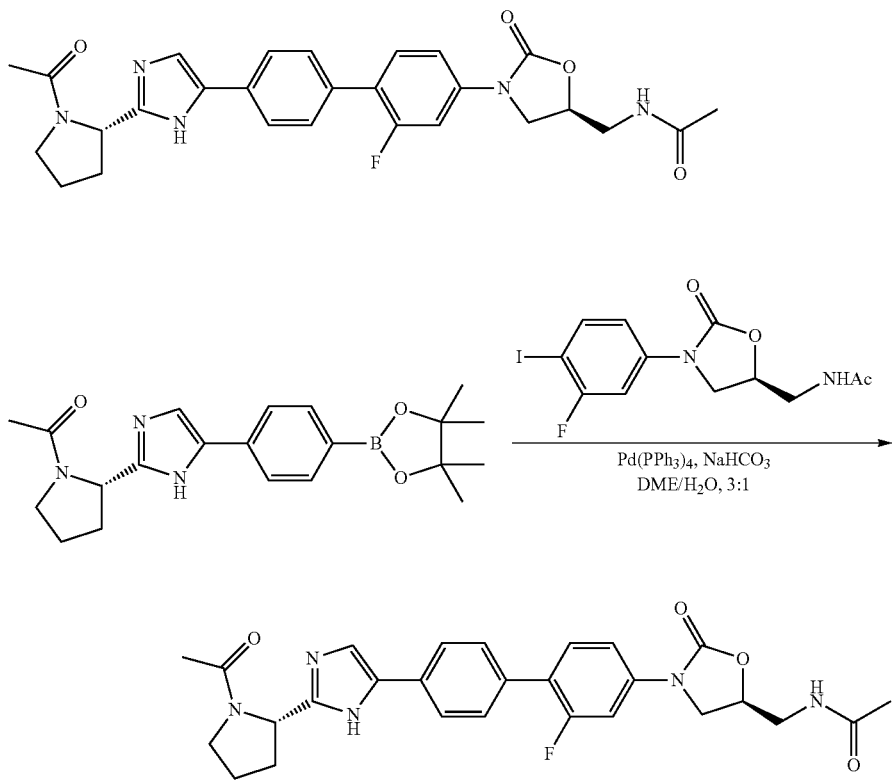

The subject compound (4 mg, 10%) was obtained from (S)-1-(2-(5-(4-(4,4,5,5-tetramethyl-1,3,2-dioxaborolan-2-yl)phenyl)-1H-imidazol 2-yl)pyrrolidin-1-yl)ethanone (30 mg, 0.078 mmol) prepared in Step (2) of Example 2, and (S)—N-((3-(3-fluoro-4-iodophenyl)-2-oxooxazolidin-5-yl)methyl)acetamide (30 mg, 0.078 mmol), according to the same method of Example 1.

$^1$H-NMR (400 MHz, DMSO): δ 7.65 (d, J=8.0 Hz, 1H), 7.50 (m, 3H), 7.40 (t, J=8.6 Hz, 1H), 7.40 (t, J=8.6 Hz, 1H), 7.21 (m, 2H), 6.74 (t, J=6.0 Hz, 1H), 5.27 (d, J=7.7 Hz, 1H), 4.84 (m, 1H), 4.08 (t, J=9.0 Hz, 1H), 3.83 (dd, J=9.0, 6.9 Hz, 1H), 3.69 (m, 2H), 3.56 (m, 1H), 2.93 (m, 1H), 2.37 (m, 1H); $^{13}$C NMR (75 MHz, CDCl$_3$): δ174.16, 171.41, 171.34, 161.42, 158.14, 154.33, 148.76, 138.24, 138.09, 133.14, 132.43, 130.68, 130.62, 129.02, 128.98, 124.94, 124.69, 124.52, 124.35, 124.34, 113.27, 124.35, 113.56, 113.52, 106.52, 106.52, 106.13, 72.06, 54.28, 53.46, 48.61, 47.41, 41.86, 29.28, 25.18, 23.06, 22.77, 21.06.

Example 15 methyl ((S)-1-((((S)-3-(2-fluoro-4'-(2-((S)-1-((methoxycarbonyl)-L-valyl)pyrrolidine-2-yl)-1H-imidazole-5-yl)-[1,1'-biphenyl]-4-yl)-2-oxooxazolidine-5-yl)methyl)amino)-3-methyl-1-oxobutane-2-yl)carbamate[Methyl ((S)-1-((((S)-3-(2-fluoro-4'-(2-((S)-1-((methoxycarbonyl)-L-valyl)pyrrolidin-2-yl)-1H-imidazol-5-yl)-[1,1'-biphenyl]-4-yl)-2-oxooxazolidin-5-yl)methyl)amino)-3-methyl-1-oxobutan-2-yl)carbamate]

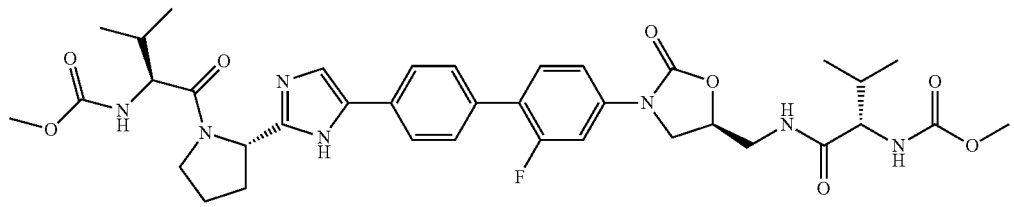

Step (1). methyl ((S)-1-((((S)-3-(3-fluoro-4-iodophenyl)-2-oxooxazolidin-5-yl)methyl)amino)-3-methyl-1-oxobutan-2-yl)carbamate

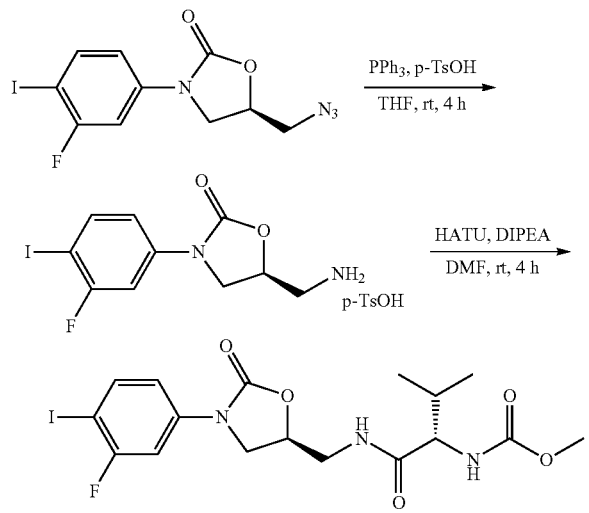

In Ar atmosphere, (R)-5-(azidomethyl)-3-(3-fluoro-4-iodophenyl)oxazolidin-2-one (3 g, 8.3 mmol) was dissolved in THF (20 mL) solution, and was added with PPh3 (2.2 g, 8.3 mmol) and p-TsOH (3.2 g, 16.6 mmol). The mixture was agitated at a room temperature for 4 hours, and the solid was filtered and washed with THF, to obtain p-toluenenesulfonic acid salt of (S)-5-(aminomethyl)-3-(3-fluoro-4-iodophenyl)oxazolidin-2-one (1.5 g, 54%). The product was used for subsequent step.

$^1$H NMR (CDCl$_3$, 300 MHz): δ8.12 (br s, 3H), 7.74 (t, J=8.3 Hz, 1H), 7.65 (dd, J=11.5, 1.9 Hz, 1H), 7.48 (d, J=7.8 Hz, 2H), 7.31 (dd, J=8.8, 2.3 Hz, 1H), 7.12 (dd, J=7.8 Hz, 2H), 4.93 (m, 1H), 4.19 (t, J=9.2 Hz, 1H), 3.82 (dd, J=9.0, 6.7 Hz, 1H), 3.26 (d, J=5.8 Hz, 2H), 2.29 (s, 3H).

In Ar atmosphere, the p-TsOH salt of amine compound (600 mg, 1.57 mmol) was dissolved in DMF (8 mL), added with (S)-2-((methoxycarbonyl)amino)-3-methylbutanoic acid (20 mg, 0.108 mmol) and HATU (72 mg, 1.88 mmol), and dropped with DIPEA (430 mg, 3.30 mmol). The mixture was agitated at a room temperature for 30 minutes and the reacting product was concentrated under vacuum. The concentrated product was added with a mixed solution of hexane and ethylacetate at a mixing ratio of 1:1 (20 mL) and was washed with H$_2$O. The aqueous solution was extracted with the mixed solution of hexane and ethylacetate at a mixing ratio of 1:1 (10 mL), and the collected organic layer was washed with brine (3×15 mL). The organic layer was dried with Na$_2$SO$_4$, filtered and concentrated under vacuum. The concentrated solution was purified with column chromatography (MC:MeOH:H$_2$O:NH$_4$OH=380:20:1:1), to obtain the subject compound (423 mg, 73%).

$^1$H NMR (CDCl$_3$, 400 MHz): δ 7.67 (t, J=7.8 Hz, 1H), 7.44 (dd, J=10.1 1.4 Hz, 1H), 7.35 (s, 1H), 7.00 (d, J=7.7 Hz, 1H) 5.42 (d, J=8.0 Hz, 1H), 4.80 (s, 1H), 4.00 (m, 2H), 3.84 (t, J=9.1 Hz, 1H), 3.80 (m, 5H), 2.80 (s, 1H), δ2.05 (m, 1H), 0.90 (dd, J=24.1, 6.4 Hz, 6H).

Step (2)

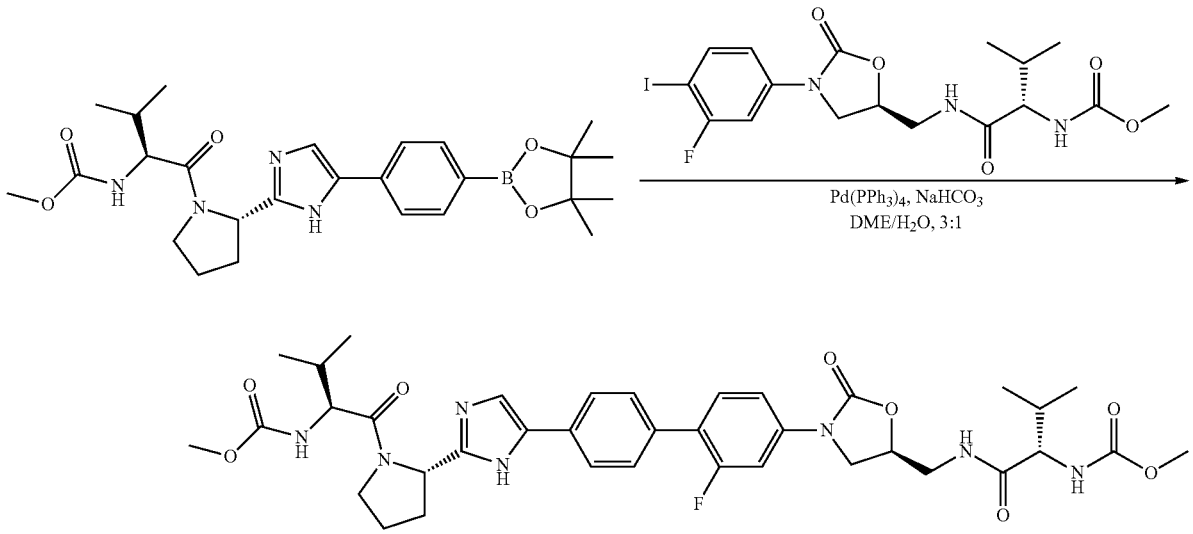

The subject compound (10 mg, 14%) was obtained from methyl ((S)-3-methyl-1-oxo-1-((S)-2-(5-(4-(4,4,5,5-tetramethyl-1,3,2-dioxaborolan-2-yl)phenyl)-1H-imidazol-2-yl)pyrrolidin-1-yl)butan-2-yl) carbamate (WO 2010148006, 50 mg, 0.1 mmol) and methyl ((S)-1-((((S)-3-(3-fluoro-4-iodophenyl)-2-oxooxazolidin-5-yl)methyl)amino)-3-methyl-1-oxobutan-2-yl)carbamate (49 mg, 0.1 mmol) prepared in Step (1), according to the same method of Example 1.

$^1$H-NMR (400 MHz, DMSO): δ 11.81 (br s, 1H), 8.38 (s, 1H), 8.34 (m, 1H), 7.86 (d, J=7.1 Hz, 2H), 7.61 (m, 3H), 7.40 (d, J=8.8 Hz, 1H), 7.30 (d, J=8.8 Hz, 1H), 7.17 (d, J=8.4 Hz, 1H), 5.10 (m, 1H), 4.92 (m, 1H), 4.79 (m, 1H), 4.24 (t, J=9.0 Hz, 1H), 4.16 (m, 1H), 4.08 (t, J=8.4 Hz, 1H), 4.03 (m, 1H), 3.93 (m, 1H), 3.67 (dd, J=14.2, 3.8 Hz, 1H), 3.55 (m, 6H), 3.48 (m, 6H), 2.16 (m, 2H), 2.00 (m, 2H), 0.89 (m, 12H).

Example 16 tert-butyl (S)-2-(5-(2'-fluoro-4'-((S)-5-(((S)-2-((methoxycarbonyl)amino)-3-methylbutanamido)methyl)-2-oxooxazolidin-3-yl)-[1,1'-biphenyl]-4-yl)-1H-imidazole-2-yl)pyrrolidine-1-carboxylate[tert-Butyl (S)-2-(5-(2'-fluoro-4'-((S)-5-(((S)-2-((methoxycarbonyl)amino)-3-methylbutanamido)methyl)-2-oxooxazolidin-3-yl)-[1,1-biphenyl]-4-yl)-1H-imidazol-2-yl)pyrrolidine-1-carboxylate]

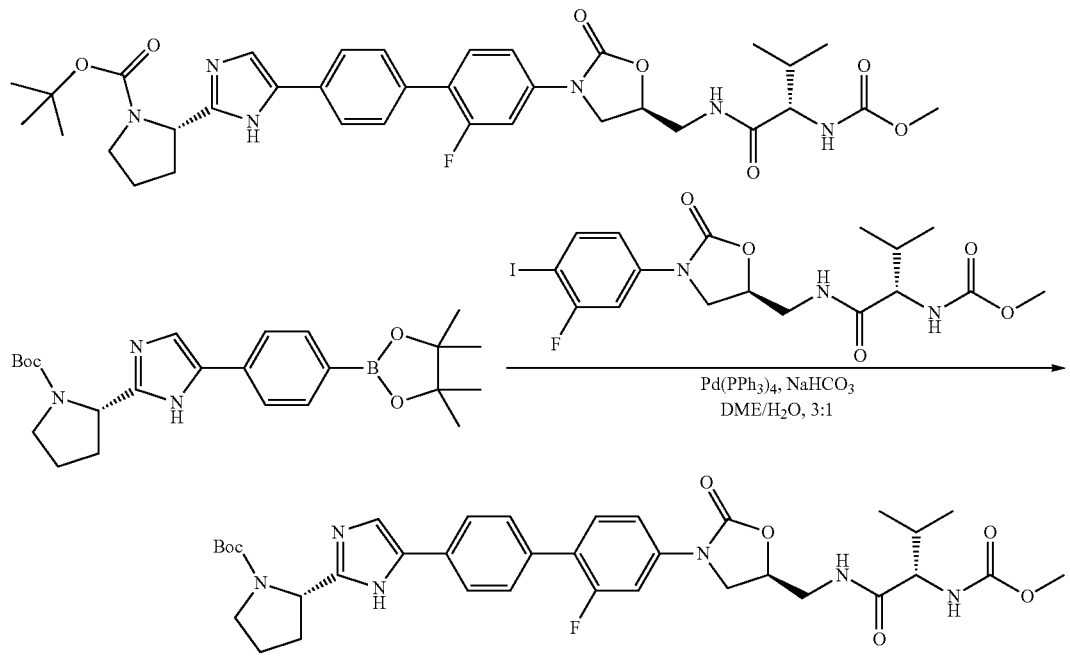

The subject compound (54 mg, 0.11 mmol) was obtained from (S)-tert-butyl 2-(5-(4-(4,4,5,5-tetramethyl-1,3,2-dioxaborolan-2-yl)phenyl)-1H-imidazol-2-yl)pyrrolidine-1-carboxylate (50 mg, 0.11 mmol) (WO 2010096462) and methyl (S)-1-((((S)-3-(3-fluoro-4-iodophenyl)-2-oxooxazolidin-5-yl)methyl)amino)-3-methyl-1-oxobutan-2-yl)carbamate (54 mg, 0.11 mmol) prepared in Step (1) of Example 15, according to the same method of Example 1.

$^1$H NMR (400 MHz, DMSO): δ11.94 (s, 1H), 8.34 (m, 1H), 7.84 (d, J=7.8 Hz, 2H), 7.75 (d, J=6.3 Hz, 1H), 7.58 (m, 5H), 7.37 (m, 1H), 7.17 (d, J=6.6 Hz, 1H), 4.78 (m, 2H), 4.24 (t, J=6.9 Hz, 1H), 4.03 (t, J=2.4 Hz, 1H), 3.95 (m, 1H), 3.93 (m, 1H), 3.82 (m, 2H), 3.54 (m, 1H), 3.45 (s, 1H), 2.04 (m, 2H), δ1.91 (m, 3H), 1.42 (s, 4H), 1.17 (s, 5H), 0.84 (m, 6H); $^{13}$C NMR (75 MHz, DMSO): δ173.84, 173.75, 173.13, 161.39, 158.11, 157.63, 157.52, 156.27, 154.40, 153.82, 149.73, 138.18, 133.04, 128.98, 124.65, 124.19, 113.66, 106.52, 106.13, 80.43, 75.08, 72.11, 69.68, 62.77, 62.66, 60.65, 54.28, 52.41, 48.18, 47.35, 41.55, 41.18, 30.91, 30.32, 30.21, 28.91, 28.51, 24.85, 19.31, 18.64, 18.09, 16.13, 16.08.

Example 17 methyl ((S)-1-((((S)-3-(4'-(2-((S)-1-acetylpyrrolidine-2-yl)-1H-imidazole-5-yl)-2-fluoro-[1,1'-biphenyl]-4-yl)-2-oxooxazolidine-5-yl)methyl)amino)-3-methyl-1-oxobutane-2-yl)carbamate[Methyl ((S)-1-((((S)-3-(4'-(2-((S)-1-acetylpyrrolidin-2-yl)-1H-imidazol-5-yl)-2-fluoro-[1,1'-biphenyl]-4-yl)-2-oxooxazolidin-5-yl)methyl)amino)-3-methyl-1-oxobutan-2-yl)carbamate]

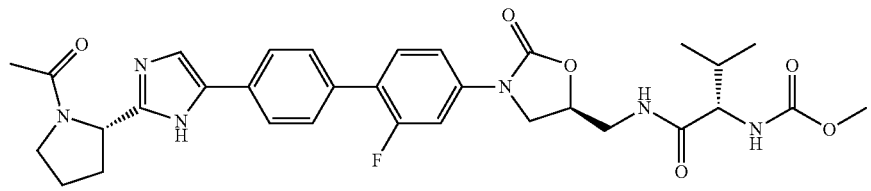

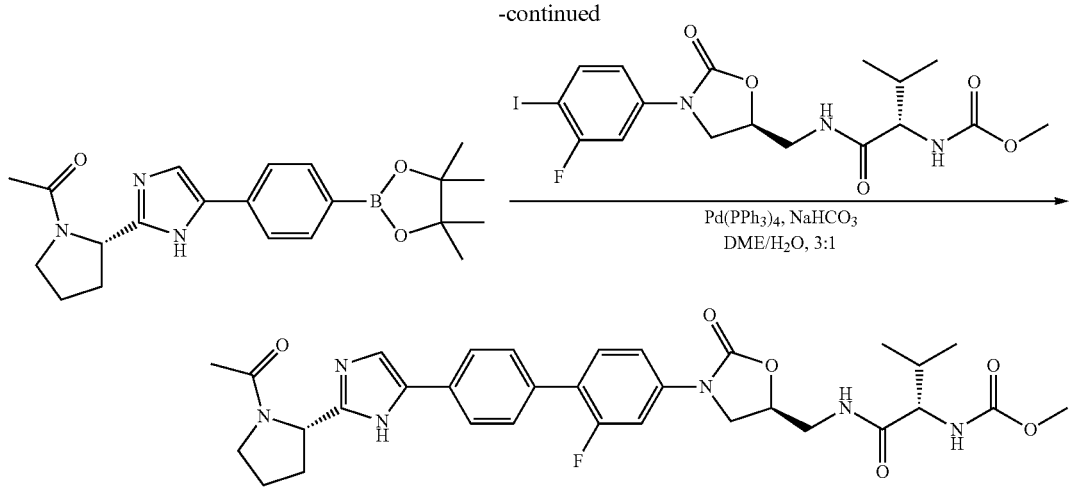

The subject compound (23 mg, 14%) was obtained from (S)-1-(2-(5-(4-(4,4,5,5-tetramethyl-1,3,2-dioxaborolan-2-yl)phenyl)-1H-imidazol-2-yl)pyrrolidin-1-yl)ethanone (100 mg, 0.26 mmol) prepared in Step (2) of Example 2 and methyl((S)-1-((((S)-3-(3-fluoro-4-iodophenyl)-2-oxooxazolidin-5-yl)methy)amino)-3-methyl-1-oxobutan-2-yl)carbamate (128 mg, 0.26 mmol) prepared in Step (1) of Example 15, according to the same method of Example 1.

$^1$H NMR (400 MHz, CDCl$_3$): δ10.45 (s, 1H), 7.84 (m, 2H), 7.49 (m, 5H), 7.29 (m, 1H), 7.25 (s, 1H), 5.92 (d, J=8.0 Hz, 1H), 5.51 (d, J=8.8 Hz, 1H), 5.30 (m, 1H), 4.96 (m, 1H), 4.36 (m, 1H), 4.22 (m, 1H), 3.98 (m, 6H), 3.73 (s, 3H), 2.28 (m, 2H), 2.07 (m, 3H), 1.08 (m, 6H); $^{13}$C NMR (75 MHz, DMSO): δ206.97, 173.30, 172.69, 161.04, 158.58, 157.15, 53.63, 130.68, 128.99, 124.87, 113.71, 106.55, 106.26, 69.46, 69.41, 62.58, 57.67, 54.49, 52.37, 48.14, 48.09, 47.92, 41.24, 31.20, 30.91, 29.69, 27.48, 25.37, 24.85, 19.23, 18.61, 17.57, 16.10.

Experimental Example

Measurement of the Oxazolidinone Compounds Activity Inhibiting the Hepatitis C Infection The inhibitory effect of the oxazolidinone compounds on HCV replicon and NS5A were HCV was tested by the method disclosed in KR-A 10-2010-0007937 or US-A 2010/0215696.

The cell lines containing replicon were prepared by preparing JFH 5a-Rluc (plasmid expressing Renilla luciferase reporter protein) RNA according to the method disclosed in the documents, introducing the JFH 5a-Rluc RNA into host cell lines (Huh7.5.1 cell line) by electroporation and infecting the host cell lines (Zhnog et al., Proc. Natl. Acad. Sci. USA, 102, 9294-9299). After the infected cell lines were cultured with or without the treatment of the oxazolidinone compound, the luciferase activity was detected to obtain the inhibitory effect of HDV replicon replication. EC$_{50}$) of the compound was determined by performing the test at various concentrations of the compound.

Experimental Example 1

Cytotoxicity Test: Filtering Process of Toxic Material

The cytotoxicity level was measured by using ToxiLight® cytotoxicity assay kit (Lonza Rockland Inc., USA) where the amount of produced ATP was detected with bioluminescence after cell lysis was caused by the compound.

Firstly, liver cancer cell lines of huh7 cell lines (Zhnog et al., Proc. Natl. Acad. Sci. USA, 102, 9294-9299) was poured in 12-well plate at a concentrate of 50,000 cells per each well. The cells on plate were cultured in the 6.0% CO$_2$ incubator (CO$_2$ Incubator 311, Forma Scientific Co. Lnc. USA.) at 37° C. for 24 hours, to fix the cells on the bottom of plate. The culture media was DMEM (Dulbecco's Modified Eagle Medium 12800-017, GIBCO Co.) as a liquid culture media used for the animal cell including 10% (v/v) FBS (Fetal Bovine Serum SH30406.02, Hyclone Co.) and 1% (v/v) of antibiotic (Penicillin/Streptomycin solution SV30010, Hyclone Co.).

The test compound was treated for the plate and the cells were cultured at 37° C. in 6.0% CO$_2$ Incubator (CO$_2$ Incubator 311, Forma Scientific Co. Lnc. USA.) for 72 hours.

To investigate the cytotoxicity, 20 μl of culture solution was taken from each well and was added to 100 μl of AK detection reagent (ToxiLight® Non-destructive Cytotoxicity Bio Assay Kit LT07-117, Lonza Co.), according to the manufacturer's manual of Cytotoxicity assay kit (Lonza). After 5 minutes, the luminescence was detected at 565 nm for 1 second by using VICTOR$^3$ (VICTOR$^{3TM}$ wallac 1420-051 Multilabel Plate Counter, PerkinElmer Inc. Boston, Mass., USA) and Wallac 1420 workstation program, and then was compared to the negative control which was treated with DMSO.

As a result, when the treated amount of the compounds of Example 1 to 17 reached 10 mM, the compounds did not show the cytotoxicity, compared to the negative control. Generally, when a compound shows the cytotoxicity at an amount of 1 mM solution, the subsequent drug development stage cannot be preceded. Thus, the compounds of the present invention can be deemed to be safe compounds without showing the cytotoxicity.

Experimental Example 2

Anti-Viral Activity Test (HCVcc, Type 2a)

The compounds of Example 1 to 17 did not show the cytotoxicity, when the compounds were treated at 1 mM in Experimental Example 1. The compounds Example 1 to 17 were tested for anti-viral activity on Hepatitis C virus, according to the method of KR10-2010-0007937 (published on Jan. 22, 2010) or US2010/0215696 (published on Aug. 26, 2010).

The cell lines containing replicon were prepared by preparing JFH 5a-Rluc (plasmid expressing Renilla luciferase reporter protein) RNA according to the method disclosed in the documents, introducing the JFH 5a-Rluc RNA into host cell lines (Huh7.5.1 cell line) by electroporation and infecting the host cell lines (Zhnog et al., Proc. Natl. Acad. Sci. USA, 102, 9294-9299). After the infected cell lines were cultured with or without the treatment of 1 mM of the oxazolidinone compounds of Examples 1 to 17, the host cell lines were obtained on 1, 2 and 3 days after treatment, and the luciferase activity produced from the host cells was measured. The result was shown in Table 1.

The luciferase activity of negative control which was not treated with the oxazolidinone compound is set to 100%. At various amounts of the oxazolidinone compounds, the luciferase activities were calculated based on the negative control to obtain the inhibition rate of HCV (%). The positive control was Interferon (INF)(Sigma, SRP4595).

TABLE 1

| Compounds of Examples | HCV inhibition rate % (1 mM) |
|---|---|
| 1 | 31.7 |
| 2 | 32.0 |
| 3 | 99.8 |
| 4 | 95.2 |
| 5 | 95.8 |
| 6 | 84.4 |
| 7 | 83.3 |
| 8 | 79.8 |
| 9 | 97.3 |
| 10 | 32.8 |
| 11 | 96.7 |
| 12 | 99.8 |
| 13 | 46.2 |
| 14 | 28.0 |
| 15 | 99.8 |
| 16 | 58.0 |
| 17 | 38.1 |
| INF 25 IU | 80.0 |

As shown in Experimental Example 1, the compounds of Example 1 to 17 did not show the cytotoxicity, when the compounds were treated at 1 mM in Experimental Example 1. Also, as shown in Table 1, the compounds showed the inhibition rate of about 31.7% to 99.8%, compared to 100% of negative control (treatment of DMSO). Accordingly, the results confirmed that the compounds of Example 1 to 17 reduced the HCV infection effectively. In particular, when Compounds of Examples 3, 9, 11, 12 and 15 were treated at a concentration of 1 nM, the remnant HCV amounts were 21.1% (78.9% of inhibition rate), 3.0% (97% of inhibition rate), 6.8% (95.2% of inhibition rate), 73% (27% of inhibition rate), or 55.7% (44.3% of inhibition rate) respectively, thereby showing excellent anti-viral activities of the compounds.

The tested compounds were evaluated for the dose-depending effect and $EC_{50}$ value (concentration of compound to inhibit the 50% of viral growth). $EC_{50}$ of the compounds of Examples 3, 9, and 15 were 0.98 nM, 17.4 nM, or 1 nM, respectively.

Thus, the compounds obtained in the Examples showed an excellent inhibitory effect on HCV and have very low risk and high safety, when they were used at an excessive amount.

What is claimed is:

1. An oxazolidinone compound represented by Formula 1, a pharmaceutically acceptable salt thereof, or a hydrate:

[Formula 1]

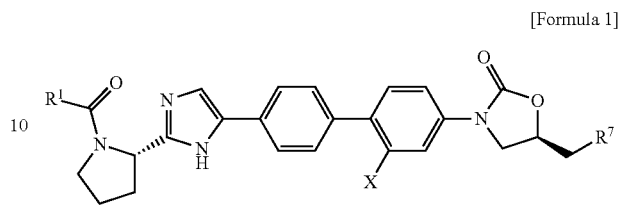

wherein, in Formula 1,
$R^1$ is $C_1$-$C_6$ alkyl, $C_1$-$C_6$ alkoxy or —CH($R^3$)NHCO$_2$R$^4$,
$R^3$ is $C_1$-$C_6$ alkyl or $C_6$-$C_{10}$ aryl,
$R^4$ is $C_1$-$C_6$ alkyl,
$R^7$ is

[two structures shown: a triazole with $R^2$ substituent, or an amide $-NHC(O)R^6$]

$R^2$ is H, $(CH_2)_n WR^5$ or $C_6$-$C_{10}$ aryl,
n is an integer of 0, 1, 2, 3 or 4,
$R^5$ is H, $C_1$-$C_6$ alkyl, benzyl, or $C_1$-$C_6$ alkyl carbonyl,
$R^6$ is $C_1$-$C_6$ alkyl, $C_1$-$C_6$ alkoxy or —CH($R^3$)NHCO$_2$R$^4$,
W is oxygen or —NH, and
X is H or F.

2. The oxazolidinone compound, a pharmaceutically acceptable salt thereof, or a hydrate according to claim 1, wherein the oxazolidinone compound is represented by Formula 2:

[Formula 2]

wherein, in Formula 2,
$R^1$ is $C_1$-$C_6$ alkyl, $C_1$-$C_6$ alkoxy or —CH($R^3$)NHCO$_2$R$^4$,
$R^2$ is H, $(CH_2)_n WR^5$ or $C_6$-$C_{10}$ aryl,
n is an integer 0, 1, 2, 3, or 4,
$R^3$ is $C_1$-$C_6$ alkyl or $C_6$-$C_{10}$ aryl,
$R^4$ is $C_1$-$C_6$ alkyl,
$R^5$ is H, $C_1$-$C_6$ alkyl, benzyl, or $C_1$-$C_6$ alkyl carbonyl,
W is oxygen or —NH, and
X is H or F.

3. The oxazolidinone compound, a pharmaceutically acceptable salt thereof, or a hydrate according to claim 2, wherein, in Formula 2,
$R^1$ is $C_1$-$C_6$ alkyl, $C_1$-$C_6$ alkoxy or —CH($R^3$)NHCO$_2$R$^4$,
$R^2$ is H, $(CH_2)_n WR^5$ or phenyl,
n is an integer of 1 to 3,
$R^3$ is isopropyl or phenyl,
$R^5$ is H, $C_1$-$C_6$ alkyl, benzyl, or $C_1$-$C_6$ alkyl carbonyl,
W is oxygen or —NH, and
X is H or F.

4. The oxazolidinone compound, a pharmaceutically acceptable salt thereof, or a hydrate according to claim 1, wherein the oxazolidinone compound is represented by Formula 3:

[Formula 3]

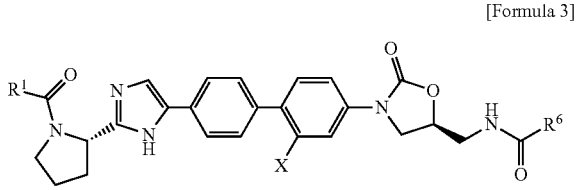

wherein in Formula 3,
R$^1$ and R$^6$ are independently C$_1$-C$_6$ alkyl, C$_1$-C$_6$ alkoxy or —CH(R$^3$)NHCO$_2$R$^4$,
R$^3$ is C$_1$-C$_6$ alkyl or C$_6$-C$_{10}$ aryl,
R$^4$ is C$_1$-C$_6$ alkyl, and
X is H or F.

5. The oxazolidinone compound, a pharmaceutically acceptable salt thereof, or a hydrate according to claim 4, wherein, in Formula 3,
R$^1$ and R$^6$ are independently C$_1$-C$_6$ alkyl, C$_1$-C$_6$ alkoxy or —CH(R$^3$)NHCO$_2$R$^4$,
R$^3$ is isopropyl or phenyl,
R$^4$ is C$_1$-C$_6$ alkyl, and
X is H or F.

6. The oxazolidinone compound, a pharmaceutically acceptable salt thereof, or a hydrate according to claim 1, wherein the oxazolidinone compound is selected from the group consisting of:
tert-butyl (S)-2-(5-(4'-((R)-5-((1H-1,2,3-triazole-1-yl)methyl)-2-oxoxazolidin-3-yl)-2'-fluoro-[1,1'-biphenyl]-4-yl)-1H-imidazole-2-yl)pyrrolidine-1-carboxylate;
(R)-5-((1H-1,2,3-triazole-1-yl)methyl)-3-(4'-(2-((S)-1-acetylpyrrolidine-2-yl)-1H-imidazole-5-yl)-2-fluoro-[1,1'-biphenyl]-4-yl)oxazolidine-2-one;
methyl ((S)-1-((S)-2-(5-(4'-((R)-5-((1H-1,2,3-triazole-1-yl)methyl)-2-oxoxazolidin-3-yl)-2'-fluoro-[1,1'-biphenyl]-4-yl)-1H-imidazole-2-yl)pyrrolidine-1-yl)-3-methyl-1-oxobutane-2-yl)carbamate;
methyl ((S)-2-((S)-2-(5-(4'-((R)-5-((1H-1,2,3-triazole-1-yl)methyl)-2-oxoxazolidin-3-yl)-2'-fluoro-[1,1'-biphenyl]-4-yl)-1H-imidazole-2-yl)pyrrolidine-1-yl)-2-oxo-1-phenylethyl)carbamate;
methyl ((S)-1-((S)-2-(5-(2'-fluoro-4'-((R)-5-((4-(hydroxymethyl)-1H-1,2,3-triazole-1-yl)methyl)-2-oxoxazolidin-3-yl)-[1,1'-biphenyl]-4-yl)-1H-imidazole-2-yl)pyrrolidine-1-yl)-3-methyl-1-oxobutane-2-yl)carbamate;
methyl ((S)-1-((S)-2-(5-(2'-fluoro-4'-((R)-5-((4-(2-hydroxyethyl)-1H-1,2,3-triazole-1-yl)methyl)-2-oxoxazolidin-3-yl)-[1,1'-biphenyl]-4-yl)-1H-imidazole-2-yl)pyrrolidine-1-yl)-3-methyl-1-oxobutane-2-yl)carbamate;
methyl ((S)-1-((S)-2-(5-(2'-fluoro-4'-((R)-5-((4-(methoxymethyl)-1H-1,2,3-triazole-1-yl)methyl)-2-oxoxazolidin-3-yl)-[1,1'-biphenyl]-4-yl)-1H-imidazole-2-yl)pyrrolidine-1-yl)-3-methyl-1-oxobutane-2-yl)carbamate;
(1-(((R)-3-(2-fluoro-4'-(2-((S)-1-((methoxycarbonyl)-L-valyl)pyrrolidine-2-yl)-1H-imidazole-5-yl)-[1,1'-biphenyl]-4-yl)-2-oxooxazolidine-5-yl)methyl)-H-1,2,3-triazole-4-yl)methyl acetate;
methyl((S)-1-((S)-2-(5-(4'-((R)-5-((4-((benzyloxy)methyl)-1H-1,2,3-triazole-1-yl)methyl)-2-oxoxazolidin-3-yl)-2'-fluoro-[1,1'-biphenyl]-4-yl)-1H-imidazole-2-yl)pyrrolidine-1-yl)-3-methyl-1-oxobutane-2-yl)carbamate;
methyl((S)-1-((S)-2-(5-(4'-((R)-5-((4-(acetamidomethyl)-1H-1,2,3-triazole-1-yl)methyl)-2-oxoxazolidin-3-yl)-2'-fluoro-[1,1'-biphenyl]-4-yl)-1H-imidazole-2-yl)pyrrolidine-1-yl)-3-methyl-1-oxobutane-2-yl)carbamate;
methyl((S)-1-((S)-2-(5-(2'-fluoro-4'-((R)-2-oxo-5-((4-phenyl-H-1,2,3-triazole-1-yl)methyl)oxazolidine-3-yl)-[1,1'-biphenyl]-4-yl)-1H-imidazole-2-yl)pyrrolidine-1-yl)-3-methyl-1-oxobutane-2-yl)carbamate;
methyl((S)-1-((S)-2-(5-(4'-((S)-5-(acetamidomethyl)-2-oxazolidine-3-yl)-2'-fluoro-[1,1'-biphenyl]-4-yl)-1H-imidazole-2-yl)pyrrolidine-1-yl)-3-methyl-1-oxobutane-2-yl)carbamate;
tert-butyl(S)-2-(5-(4'-((S)-5-(acetamidomethyl)-2-oxoxazolidine-3-yl)-2'-fluoro-[1,1'-biphenyl]-4-yl)-1H-imidazole-2-yl)pyrrolidine-1-carboxylate;
N—(((S)-3-(4'-(2-((S)-1-acetylpyrrolidine-2-yl)-1H-imidazole-5-yl)-2-fluoro-[1,1'-biphenyl]-4-yl)-2-oxooxazolidine-5-yl)methyl)acetamide;
methyl ((S)-1-((((S)-3-(2-fluoro-4'-(2-((S)-1-((methoxycarbonyl)-L-valyl)pyrrolidine-2-yl)-1H-imidazole-5-yl)-[1,1'-biphenyl]-4-yl)-2-oxooxazolidine-5-yl)methyl)amino)-3-methyl-1-oxobutane-2-yl)carbamate;
tert-butyl (S)-2-(5-(2'-fluoro-4'-((S)-5-(((S)-2-((methoxycarbonyl)amino)-3-methylbutanamido)methyl)-2-oxoxazolidin-3-yl)-[1,1'-biphenyl]-4-yl)-1H-imidazole-2-yl)pyrrolidine-1-carboxylate; and
methyl((S)-1-((((S)-3-(4'-(2-((S)-1-acetylpyrrolidine-2-yl)-1H-imidazole-5-yl)-2-fluoro-[1,1'-biphenyl]-4-yl)-2-oxooxazolidine-5-yl)methyl)amino)-3-methyl-1-oxobutane-2-yl)carbamate.

7. The oxazolidinone compound, a pharmaceutically acceptable salt thereof, or a hydrate according to claim 1, wherein the pharmaceutically acceptable salt is a salt of organic acid or inorganic acid selected from the group consisting of hydrochloric acid, hydrobromic acid, sulfuric acid, a phosphoric acid, nitric acid, acetic acid, glycolic acid, lactic acid, pyruvic acid, malonic acid, succinic acid, glutaric acid, fumaric acid, malic acid, a mandelic acid, tartaric acid, citric acid, ascorbic acid, palmitic acid, maleic acid, hydroxymaleic acid, benzoic acid, hydroxybenzoic acid, phenylacetic acid, cinnamic acid, salicylic acid, methanesulfonic acid, benzene sulfonic acid and toluene sulfonic acid.

8. A method of preparing an oxazolidinone compound represented by Formula 2, or a pharmaceutically acceptable salt thereof, comprising a step of reacting the compound of Formula 4 and the compound of Formula 5:

[Formula 2]

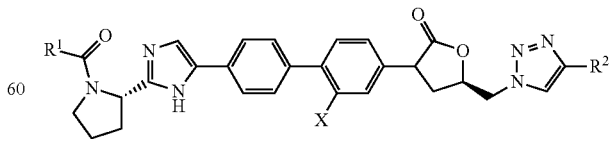

wherein, in Formula 2,
R$^1$ is C$_1$-C$_6$ alkyl, C$_1$-C$_6$ alkoxy or —CH(R$^3$)NHCO$_2$R$^4$,
R$^2$ is H, (CH$_2$)$_n$WR$^5$ or C$_6$-C$_{10}$ aryl,
n is an integer 0, 1, 2, 3 or 4, $R^3$ is $C_1$-$C_6$ alkyl or $C_6$-$C_{10}$ aryl,
$R^4$ is $C_1$-$C_6$ alkyl,
$R^5$ is H, $C_1$-$C_6$ alkyl, benzyl, or $C_1$-$C_6$ alkyl carbonyl,
W is oxygen or —NH, and
X is H or F,

[Formula 4]

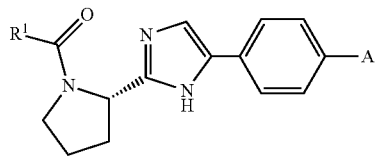

wherein Formula 4,
$R^1$ is $C_1$-$C_6$ alkyl, $C_1$-$C_6$ alkoxy or —CH($R^3$)NHCO$_2$R$^4$,
$R^3$ is $C_1$-$C_6$ alkyl or $C_6$-$C_{10}$ aryl,
$R^4$ is $C_1$-$C_6$ alkyl, and
A is a halogen, boronic acid [B(OH)$_2$], $C_1$-$C_6$ alkyl, or pinacol borate,

[Formula 5]

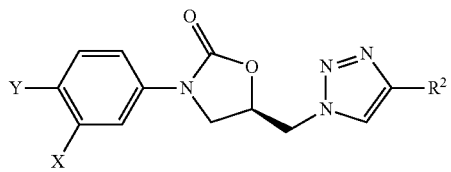

wherein, in Formula 5,
$R^2$ is H, (CH$_2$)$_n$WR$^5$ or $C_6$-$C_{10}$ aryl,
n is an integer 0, 1, 2, 3, or 4,
$R^5$ is H, $C_1$-$C_6$ alkyl, benzyl, or $C_1$-$C_6$ alkyl carbonyl,
X is H or F,
W is oxygen or —NH, and
A is a halogen, boronic acid [B(OH)$_2$], $C_1$-$C_6$ alkyl, or pinacol borate.

9. The method of preparing an oxazolidinone compound represented by Formula 2, or a pharmaceutically acceptable salt thereof according to claim 8, wherein the method comprises the steps of:
(1) reacting the compound of Formula 4 and the compound of Formula 5 according to the standard Suzuki binding reaction, to produce the compound of Formula 7;

[Formula 7]

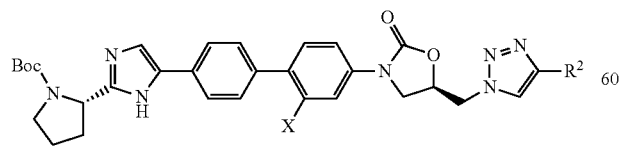

(2) deprotecting Boc protecting group in the compound of Formula 7 obtained in step (1), to produce the compound of Formula 8; and

[Formula 8]

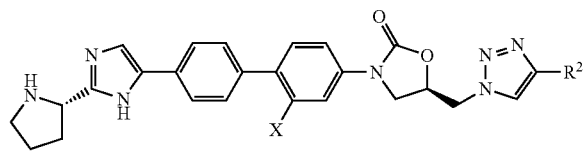

(3) preparing the compound of Formula 2 by reacting the compound of Formula 8, obtained in step (2), with a carboxylic acid compound of the formula,

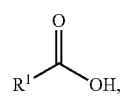

according to the standard amide binding:
wherein,
$R^2$ is H, (CH$_2$)$_n$WR$^5$ or $C_6$-$C_{10}$ aryl,
n is an integer 0, 1, 2, 3, or 4,
$R^5$ is H, $C_1$-$C_6$ alkyl, benzyl, or $C_1$-$C_6$ alkyl carbonyl,
W is oxygen, or —NH,
X is H or F, and
$R^1$ is $C_1$-$C_6$ alkyl, $C_1$-$C_6$ alkoxy or —CH($R^3$)NHCO$_2$R$^4$.

10. A method of preparing an oxazolidinone compound represented by Formula 3, or a pharmaceutically acceptable salt thereof, comprising a step of reacting the compound of Formula 4 and the compound of Formula 9:

[Formula 3]

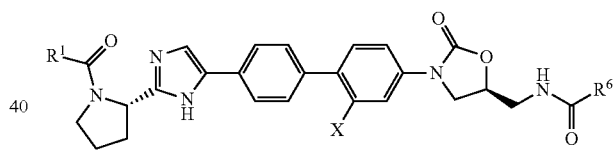

wherein, in Formula 3,
$R^1$ or $R^6$ is independently $C_1$-$C_6$ alkyl, $C_1$-$C_6$ alkoxy or —CH($R^3$)NHCO$_2$R$^4$,
$R^3$ is $C_1$-$C_6$ alkyl or $C_6$-$C_{10}$ aryl,
$R^4$ is $C_1$-$C_6$ alkyl, and
X is H or F,

[Formula 4]

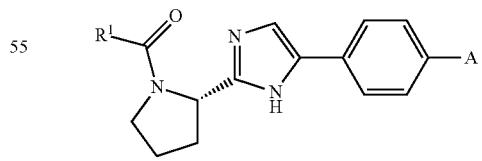

wherein, in Formula 4,
$R^1$ is $C_1$-$C_6$ alkyl, $C_1$-$C_6$ alkoxy or —CH($R^3$)NHCO$_2$R$^4$,
$R^3$ is $C_1$-$C_6$ alkyl or $C_6$-$C_{10}$ aryl,
$R^4$ is $C_1$-$C_6$ alkyl, and
A is a halogen, boronic acid [B(OH)$_2$], $C_1$-$C_6$ alkyl, or pinacol borate,

[Formula 9]

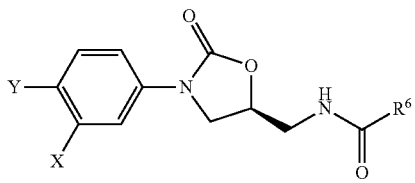

wherein, in Formula 9,
$R^6$ is $C_1$-$C_6$ alkyl, $C_1$-$C_6$ alkoxy or —CH($R^3$)NHCO$_2$R$^4$,
$R^3$ is $C_1$-$C_6$ alkyl or $C_6$-$C_{10}$ aryl,
$R^4$ is $C_1$-$C_6$ alkyl,
X is H or F, and
A is a halogen, boronic acid [B(OH)$_2$], $C_1$-$C_6$ alkyl, or pinacol borate.

11. The method of preparing an oxazolidinone compound represented by Formula 3, or a pharmaceutically acceptable salt thereof according to claim 10, wherein the method comprises the steps of:

(1) reacting the compound of Formula 4 and the compound of Formula 9 according to the standard Suzuki binding reaction, to produce the compound of Formula 10;

[Formula 10]

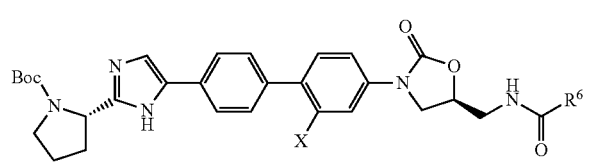

(2) deprotecting Boc protecting group in the compound of Chemical Formula 10 obtained in step (1), to produce the compound of Formula 11; and

[Formula 11]

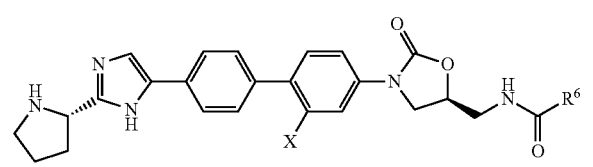

(3) preparing the compound of Formula 2-3 by reacting the compound of Formula 11 obtained in step (2), with a carboxylic acid compound of the formula,

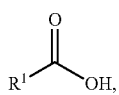

according to the standard amide binding:
wherein,
$R^6$ is $C_1$-$C_6$ alkyl, $C_1$-$C_6$ alkoxy or —CH($R^3$)NHCO$_2$R$^4$,
$R^3$ is $C_1$-$C_6$ alkyl or $C_6$-$C_{10}$ aryl,
$R^4$ is $C_1$-$C_6$ alkyl,
X is H or F, and
$R^1$ is $C_1$-$C_6$ alkyl, $C_1$-$C_6$ alkoxy or —CH($R^3$)NHCO$_2$R$^4$.

12. A method of treating a disease caused by Hepatitis C virus (HCV) infection, comprising administering the oxazolidinone compound, pharmaceutically acceptable salt thereof, or hydrate according to claim 1, to a subject in need, wherein the disease is selected from Hepatitis C infection, cirrhosis, or Hepatocellular carcinoma.

13. The method according to claim 12, wherein the oxazolidinone compounds, pharmaceutically acceptable salt thereof, or hydrate is contained at an amount of 0.5 to 10 wt % with respect to the total weight of a composition comprising the oxazolidinone compound, pharmaceutically acceptable salt thereof, or hydrate.

14. The method according to claim 12, wherein the oxazolidinone compound is represented by Formula 2:

[Formula 2]

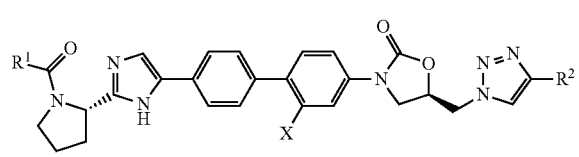

wherein, in Formula 2,
$R^1$ is $C_1$-$C_6$ alkyl, $C_1$-$C_6$ alkoxy or —CH($R^3$)NHCO$_2$R$^4$,
$R^2$ is H, (CH$_2$)$_n$WR$^5$ or $C_6$-$C_{10}$ aryl,
n is an integer 0, 1, 2, 3, or 4,
$R^3$ is $C_1$-$C_6$ alkyl or $C_6$-$C_{10}$ aryl,
$R^4$ is $C_1$-$C_6$ alkyl,
$R^5$ is H, $C_1$-$C_6$ alkyl, benzyl, or $C_1$-$C_6$ alkyl carbonyl,
W is oxygen or —NH, and
X is H or F.

15. The method according to claim 12, wherein the oxazolidinone compounds is represented by Formula 2, wherein
$R^1$ is $C_1$-$C_6$ alkyl, $C_1$-$C_6$ alkoxy or —CH($R^3$)NHCO$_2$R$^4$,
$R^2$ is H, (CH$_2$)$_n$WR$^5$ or phenyl,
n is an integer of 1 to 3,
$R^3$ is isopropyl or phenyl,
$R^5$ is H, $C_1$-$C_6$ alkyl, benzyl, or $C_1$-$C_6$ alkyl carbonyl,
W is oxygen or —NH, and
X is H or F.

16. The method according to claim 12, wherein the oxazolidinone compound is represented by Formula 3:

[Formula 3]

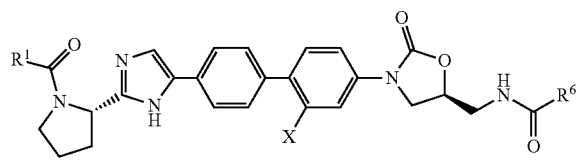

wherein, in Formula 3,
$R^1$ or $R^6$ is independently $C_1$-$C_6$ alkyl, $C_1$-$C_6$ alkoxy or —CH($R^3$)NHCO$_2$R$^4$,
$R^3$ is $C_1$-$C_6$ alkyl or $C_6$-$C_{10}$ aryl,
$R^4$ is $C_1$-$C_6$ alkyl, and
X is H or F.

17. The method according to claim 16, wherein, in Formula 3,
$R^1$ or $R^6$ is independently $C_1$-$C_6$ alkyl, $C_1$-$C_6$ alkoxy or —CH($R^3$)NHCO$_2$R$^4$, R³ is isopropyl or phenyl,
R⁴ is C₁-C₆ alkyl, and
X is H or F.

18. The method according to claim 12, wherein the oxazolidinone compound is selected from the group consisting of:

tert-butyl (S)-2-(5-(4'-((R)-5-((1H-1,2,3-triazole-1-yl)methyl)-2-oxoxazolidin-3-yl)-2'-fluoro-[1,1'-biphenyl]-4-yl)-1H-imidazole-2-yl)pyrrolidine-1-carboxylate;

(R)-5-((1H-1,2,3-triazole-1-yl)methyl)-3-(4'-(2-((S)-1-acetylpyrrolidine-2-yl)-1H-imidazole-5-yl)-2-fluoro-[1,1'-biphenyl]-4-yl)oxazolidine-2-one;

methyl ((S)-1-((S)-2-(5-(4'-((R)-5-((1H-1,2,3-triazole-1-yl)methyl)-2-oxoxazolidin-3-yl)-2'-fluoro-[1,1'-biphenyl]-4-yl)-1H-imidazole-2-yl)pyrrolidine-1-yl)-3-methyl-1-oxobutane-2-yl)carbamate;

methyl ((S)-2-((S)-2-(5-(4'-((R)-5-((1H-1,2,3-triazole-1-yl)methyl)-2-oxoxazolidin-3-yl)-2'-fluoro-[1,1'-biphenyl]-4-yl)-1H-imidazole-2-yl)pyrrolidine-1-yl)-2-oxo-1-phenylethyl)carbamate;

methyl ((S)-1-((S)-2-(5-(2'-fluoro-4'4(R)-5 #4-(hydroxymethyl)-1H-1,2,3-triazole-1-yl)methyl)-2-oxoxazolidin-3-yl)-[1,1'-biphenyl]-4-yl)-1H-imidazole-2-yl)pyrrolidine-1-yl)-3-methyl-1-oxobutane-2-yl) carbamate;

methyl ((S)-1-((S)-2-(5-(2'-fluoro-4'-((R)-5-((4-(2-hydroxyethyl)-1H-1,2,3-triazole-1-yl)methyl)-2-oxoxazolidin-3-yl)-[1,1'-biphenyl]-4-yl)-1H-imidazole-2-yl)pyrrolidine-1-yl)-3-methyl-1-oxobutane-2-yl) carbamate;

methyl ((S)-1-((S)-2-(5-(2'-fluoro-4'-((R)-5-((4-(methoxymethyl)-1H-1,2,3-triazole-1-yl)methyl)-2-oxoxazolidin-3-yl)-[1,1'-biphenyl]-4-yl)-1H-imidazole-2-yl)pyrrolidine-1-yl)-3-methyl-1-oxobutane-2-yl)carbamate;

(1-(((R)-3-(2-fluoro-4'-(2-((S)-1-((methoxycarbonyl)-L-valyl)pyrrolidine-2-yl)-1H-imidazole-5-yl)-[1,1'-biphenyl]-4-yl)-2-oxooxazolidine-5-yl)methyl)-1H-1,2,3-triazole-4-yl)methyl acetate;

methyl ((S)-1-((S)-2-(5-(4'4-((R)-5-((4-((benzyloxy)methyl)-1H-1,2,3-triazole-1-yl)methyl)-2-oxoxazolidin-3-yl)-2'-fluoro-[1,1'-biphenyl]-4-yl)-1H-imidazole-2-yl)pyrrolidine-1-yl)-3-methyl-1-oxobutane-2-yl)carbamate;

methyl ((S)-1-((S)-2-(5-(4'-((R)-5-((4-(acetamidomethyl)-1H-1,2,3-triazole-1-yl)methyl)-2-oxoxazolidin-3-yl)-2'-fluoro-[1,1'-biphenyl]-4-yl)-1H-imidazole-2-yl)pyrrolidine-1-yl)-3-methyl-1-oxobutane-2-yl) carbamate;

methyl ((S)-1-((s)-2-(5-(2'-fluoro-4'-((R)-2-oxo-5-((4-phenyl-1H-1,2,3-triazole-1-yl)methyl)oxazolidine-3-yl)-[1,1'-biphenyl]-4-yl)-1H-imidazole-2-yl)pyrrolidine-1-yl)-3-methyl-1-oxobutane-2-yl)carbamate;

methyl ((S)-1-((S)-2-(5-(4'-((S)-5-(acetamidomethyl)-2-oxazolidine-3-yl)-2'-fluoro-[1,1'-biphenyl]-4-yl)-1H-imidazole-2-yl)pyrrolidine-1-yl)-3-methyl-1-oxobutane-2-yl)carbamate;

tert-butyl (S)-2-(5-(4'-((S)-5-(acetamidomethyl)-2-oxoxazolidin-3-yl)-2'-fluoro-[1,1'-biphenyl]-4-yl)-1H-imidazole-2-yl)pyrrolidine-1-carboxylate;

N-(((S)-3-(4'-(2-((S)-1-acetylpyrrolidine-2-yl)-1H-imidazole-5-yl)-2-fluoro-[1,1'-biphenyl]-4-yl)-2-oxooxazolidine-5-yl)methyl)acetamide;

methyl ((S)-1-((((S)-3-(2-fluoro-4'-(2-((S)-1-((methoxycarbonyl)-L-valyl)pyrrolidine-2-yl)-1H-imidazole-5-yl)-[1,1'-biphenyl]-4-yl)-2-oxooxazolidine-5-yl)methyl)amino)-3-methyl-1-oxobutane-2-yl)carbamate;

tert-butyl (5)-2-(5-(2'-fluoro-4'-((S)-5-(((S)-2-((methoxycarbonyl)amino)-3-methylbutanamido)methyl)-2-oxoxazolidin-3-yl)-[1,1'-biphenyl]-4-yl)-1H-imidazole-2-yl)pyrrolidine-1-carboxylate; and methyl ((S)-1-((((S)-3-(4'-(2-((S)-1-acetylpyrrolidine-2-yl)-1H-imidazole-5-yl)-2-fluoro-[1,1'-biphenyl]-4-yl)-2-oxooxazolidine-5-yl)methyl)amino)-3-methyl-1-oxobutane-2-yl)carbamate.

19. A method of inhibiting a growth or an activity of HCV (Hepatitis C virus), comprising a step of treating with an oxazolidinone compound, pharmaceutically acceptable salt thereof, or hydrate according to claim 1.

20. The method according to claim 19, wherein the oxazolidinone compound, pharmaceutically acceptable salt thereof, or hydrate is contained at an amount of 0.5 to 10 wt % with respect to the total weight of a composition comprising the oxazolidinone compound, pharmaceutically acceptable salt thereof, or hydrate.

* * * * *